US008376985B2

(12) United States Patent  
Pongpairochana et al.

(10) Patent No.: US 8,376,985 B2
(45) Date of Patent: Feb. 19, 2013

(54) HAND-HELD ELECTRONICALLY CONTROLLED INJECTION DEVICE FOR INJECTING LIQUID MEDICATIONS

(75) Inventors: Vincent Pongpairochana, La Conversion (CH); Timothy John MacLean, Bath and South East Somerset (GB); Robert Prasser, Althofen (AT); Gerhard Lauchard, Silberegg (AT); Werner Wurmbauer, Klagenfurt (AT); Gerhard Kogler, Althofen (AT)

(73) Assignee: Ares Trading S.A., Aubonne (CH)

( * ) Notice: Subject to any disclaimer, the term of this patent is extended or adjusted under 35 U.S.C. 154(b) by 0 days.

(21) Appl. No.: 13/096,890

(22) Filed: Apr. 28, 2011

(65) Prior Publication Data

US 2011/0201998 A1    Aug. 18, 2011

Related U.S. Application Data

(63) Continuation of application No. 12/717,344, filed on Mar. 4, 2010, now Pat. No. 7,967,784, which is a continuation of application No. 10/589,465, filed as application No. PCT/EP2005/050711 on Feb. 17, 2005, now Pat. No. 7,704,231.

(30) Foreign Application Priority Data

Feb. 18, 2004   (EP) ..................................... 04100647

(51) Int. Cl.
*A61M 31/00*   (2006.01)
(52) U.S. Cl. ........................................................ 604/67
(58) Field of Classification Search .................. 604/134
See application file for complete search history.

(56) References Cited

U.S. PATENT DOCUMENTS

| 4,150,672 A | 4/1979 | Whitney et al. |
| 4,273,122 A | 6/1981 | Whitney et al. |
| 4,373,527 A | 2/1983 | Fischell |
| 4,435,173 A | 3/1984 | Siposs et al. |
| 4,493,704 A | 1/1985 | Beard et al. |
| 4,529,401 A | 7/1985 | Leslie et al. |
| 4,573,994 A | 3/1986 | Fischell et al. |
| 4,627,835 A | 12/1986 | Fenton, Jr. |
| 4,950,246 A | 8/1990 | Muller |
| 4,959,056 A | 9/1990 | Dombrowski et al. |
| 4,976,696 A | 12/1990 | Sanderson et al. |

(Continued)

FOREIGN PATENT DOCUMENTS

| DE | 2950140 | 6/1981 |
| DE | 3824217 | 1/1990 |

(Continued)

OTHER PUBLICATIONS

International Search Report for International Application No. PCT/EP2005/050711, mailed Oct. 11, 2005.

*Primary Examiner* — Nicholas Lucchesi
*Assistant Examiner* — Jason Flick
(74) *Attorney, Agent, or Firm* — Nixon Peabody LLP

(57) ABSTRACT

A medication delivery device includes a housing, a door coupled to the housing and moveable between a closed position and an open position. The door permits insertion of a medication container, containing liquid medication, into the housing in the open position. A door opening mechanism is coupled to the door. A push member is axially moveable between a retracted position and a non-retracted position and located external to the medication container. The push member enters the medication container and pushes the liquid medication out of the medication container. A lock mechanism is coupled to the door opening mechanism and prevents opening of the door when the push member is in the non-retracted position inside the medication container, wherein the lock mechanism automatically unlocks the door opening mechanism when the push member is in the retracted position.

7 Claims, 21 Drawing Sheets

U.S. PATENT DOCUMENTS

| | | | |
|---|---|---|---|
| 4,978,335 A | 12/1990 | Arthur, III | |
| 5,034,004 A | 7/1991 | Crankshaw | |
| 5,106,375 A | 4/1992 | Conero | |
| 5,131,816 A | 7/1992 | Brown et al. | |
| 5,139,484 A | 8/1992 | Hazon et al. | |
| 5,232,449 A | 8/1993 | Stern et al. | |
| 5,254,096 A | 10/1993 | Rondelet et al. | |
| 5,269,762 A | 12/1993 | Armbruster et al. | |
| 5,330,431 A | 7/1994 | Herskowitz | |
| 5,354,287 A | 10/1994 | Wacks et al. | |
| 5,360,410 A | 11/1994 | Wacks et al. | |
| 5,545,140 A | 8/1996 | Conero et al. | |
| 5,573,515 A | 11/1996 | Wilson et al. | |
| 5,584,815 A | 12/1996 | Pawelka et al. | |
| 5,628,309 A | 5/1997 | Brown | |
| 5,651,775 A | 7/1997 | Walker et al. | |
| 5,658,133 A | 8/1997 | Anderson et al. | |
| 5,662,612 A | 9/1997 | Niehoff | |
| 5,681,285 A | 10/1997 | Ford et al. | |
| 5,693,027 A | 12/1997 | Hansen et al. | |
| 5,697,916 A | 12/1997 | Schraga | |
| 5,704,922 A | 1/1998 | Brown | |
| 5,720,733 A | 2/1998 | Brown | |
| 5,728,074 A | 3/1998 | Castellano et al. | |
| 5,782,814 A | 7/1998 | Brown et al. | |
| 5,792,117 A | 8/1998 | Brown | |
| 5,882,343 A | 3/1999 | Wilson et al. | |
| 5,928,197 A | 7/1999 | Niehoff | |
| 5,928,201 A | 7/1999 | Poulsen et al. | |
| 5,947,934 A | 9/1999 | Hansen et al. | |
| 5,954,700 A | 9/1999 | Kovelman | |
| 5,997,513 A | 12/1999 | Smith et al. | |
| 6,019,745 A | 2/2000 | Gray | |
| 6,045,537 A | 4/2000 | Klitmose | |
| 6,110,152 A | 8/2000 | Kovelman | |
| 6,159,161 A | 12/2000 | Hodosh | |
| 6,171,276 B1 | 1/2001 | Lippe et al. | |
| 6,203,530 B1 | 3/2001 | Stewart, Sr. | |
| 6,248,090 B1 | 6/2001 | Jensen et al. | |
| 6,269,340 B1 | 7/2001 | Ford et al. | |
| 6,277,098 B1 | 8/2001 | Klitmose et al. | |
| 6,340,357 B1 | 1/2002 | Poulsen et al. | |
| 6,406,460 B1 | 6/2002 | Hogan | |
| 6,423,035 B1 | 7/2002 | Das et al. | |
| 6,547,755 B1 | 4/2003 | Lippe et al. | |
| 6,585,698 B1 | 7/2003 | Packman et al. | |
| 6,599,272 B1 | 7/2003 | Hjertman et al. | |
| 6,641,566 B2 | 11/2003 | Douglas et al. | |
| 6,645,177 B1 | 11/2003 | Shearn | |
| 6,685,678 B2 | 2/2004 | Evans et al. | |
| 6,830,560 B1 | 12/2004 | Gross et al. | |
| 6,942,646 B2 | 9/2005 | Langley et al. | |
| 6,954,697 B1 | 10/2005 | Smith | |
| 6,972,007 B2 | 12/2005 | Geiser et al. | |
| 6,997,906 B2 | 2/2006 | Langley et al. | |
| 7,001,360 B2 | 2/2006 | Veasey et al. | |
| 7,008,405 B2 | 3/2006 | Langley et al. | |
| 7,052,484 B2 | 5/2006 | Veasey et al. | |
| 7,704,231 B2 | 4/2010 | Pongpairochana et al. | |
| 7,967,784 B2 | 6/2011 | Pongpairochana et al. | |
| 2002/0030002 A1 | 3/2002 | Verkaart et al. | |
| 2002/0032429 A1 | 3/2002 | Hjertman et al. | |
| 2002/0128606 A1 | 9/2002 | Cowan et al. | |
| 2002/0133113 A1 | 9/2002 | Madsen et al. | |
| 2003/0060768 A1 | 3/2003 | Kiyatake et al. | |
| 2003/0065287 A1* | 4/2003 | Spohn et al. | 604/154 |
| 2003/0093036 A1 | 5/2003 | Crossman et al. | |
| 2003/0153868 A1 | 8/2003 | Azizi et al. | |
| 2003/0163090 A1* | 8/2003 | Blomquist et al. | 604/154 |
| 2004/0176729 A1 | 9/2004 | Langley et al. | |
| 2004/0178255 A1 | 9/2004 | Eich et al. | |
| 2004/0210199 A1 | 10/2004 | Atterbury et al. | |
| 2004/0249348 A1 | 12/2004 | Wimpenny et al. | |
| 2004/0260247 A1 | 12/2004 | Veasey et al. | |
| 2005/0004529 A1 | 1/2005 | Veasey et al. | |
| 2005/0090781 A1 | 4/2005 | Baba et al. | |
| 2005/0107899 A1 | 5/2005 | Steffen | |
| 2005/0107923 A1 | 5/2005 | Vanderveen | |
| 2005/0113765 A1 | 5/2005 | Veasey et al. | |
| 2005/0148938 A1 | 7/2005 | Blomquist | |
| 2005/0151652 A1 | 7/2005 | Frasch | |
| 2005/0182360 A1 | 8/2005 | Yeandel et al. | |
| 2005/0251103 A1 | 11/2005 | Steffen et al. | |
| 2007/0142776 A9 | 6/2007 | Kovelman et al. | |

FOREIGN PATENT DOCUMENTS

| | | |
|---|---|---|
| DE | 4420232 | 12/1995 |
| DE | 19643913 | 9/1997 |
| DE | 19643813 | 4/1998 |
| DE | 10236669 | 2/2004 |
| EP | 0319279 | 6/1989 |
| EP | 0362484 | 4/1990 |
| EP | 1219312 | 7/2002 |
| EP | 1462134 | 9/2004 |
| EP | 1593403 | 11/2005 |
| EP | 1666080 | 6/2006 |
| GB | 809773 | 3/1959 |
| GB | 2262452 | 6/1993 |
| JP | 2004-100838 | 4/2004 |
| WO | 93/12726 | 7/1993 |
| WO | 95/09021 | 4/1995 |
| WO | 96/38190 | 12/1996 |
| WO | 97/14459 | 4/1997 |
| WO | 99/65548 | 12/1999 |
| WO | 02/11792 | 2/2002 |
| WO | 02/081011 | 10/2002 |
| WO | 03/047663 | 6/2003 |
| WO | 03/057286 | 7/2003 |
| WO | 03/077968 | 9/2003 |
| WO | 2004/006995 | 1/2004 |
| WO | 2004/047891 | 6/2004 |
| WO | 2004/084795 | 10/2004 |
| WO | 2005/000384 | 1/2005 |
| WO | 2005/004954 | 1/2005 |
| WO | 2005/032449 | 4/2005 |
| WO | 2006/015501 | 2/2006 |
| WO | 2006/058883 | 6/2006 |
| WO | 2006/069455 | 7/2006 |

\* cited by examiner

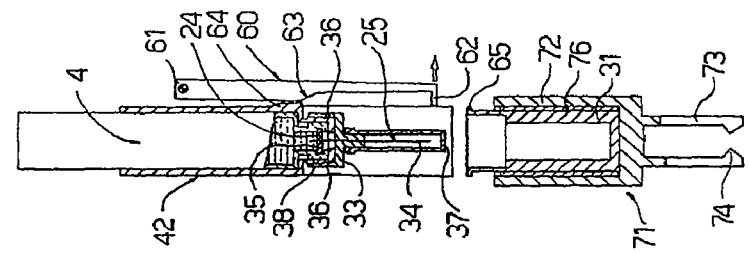
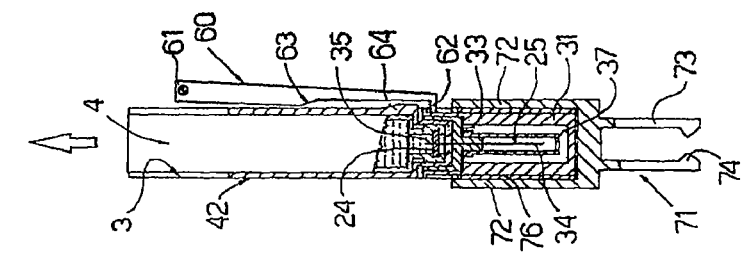
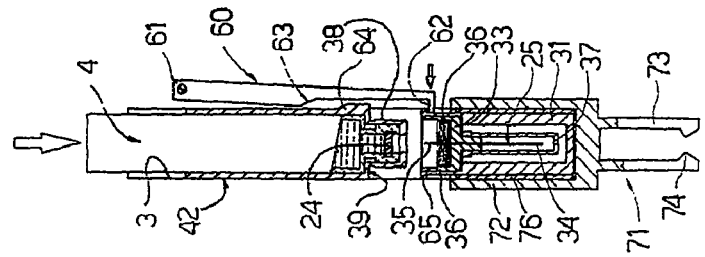
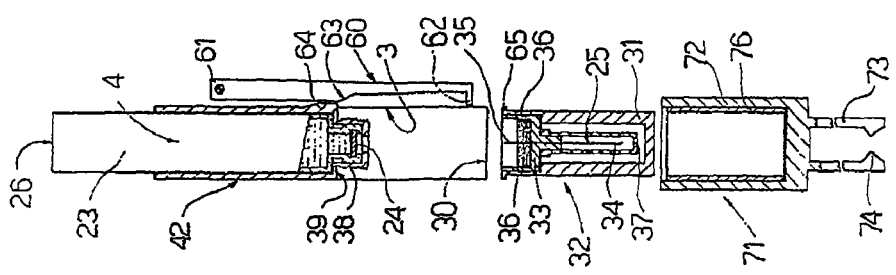

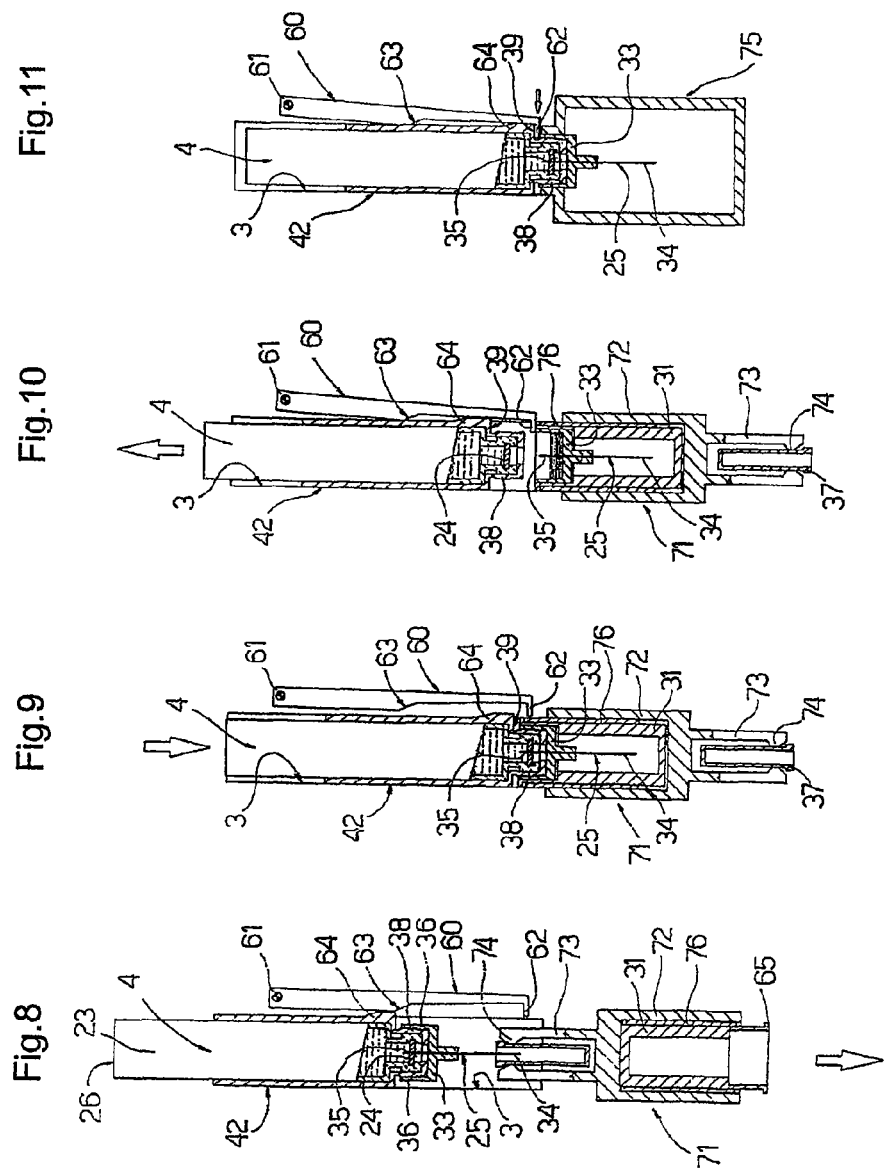

Fig.21
Fig.22
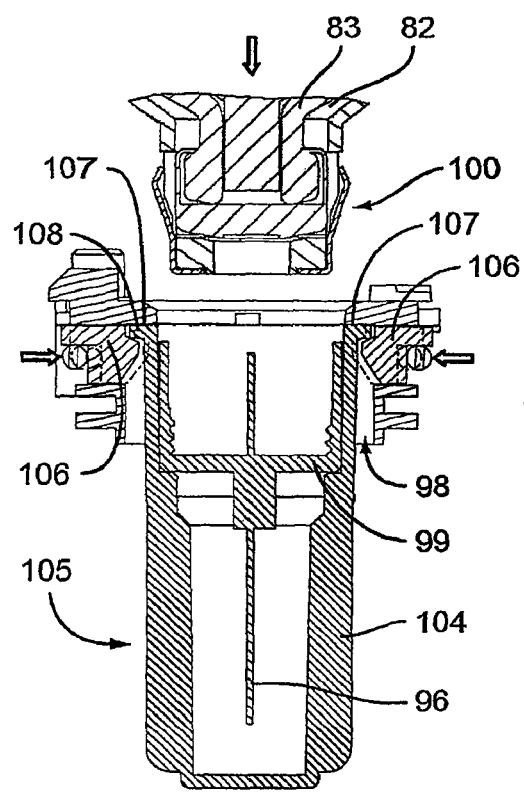
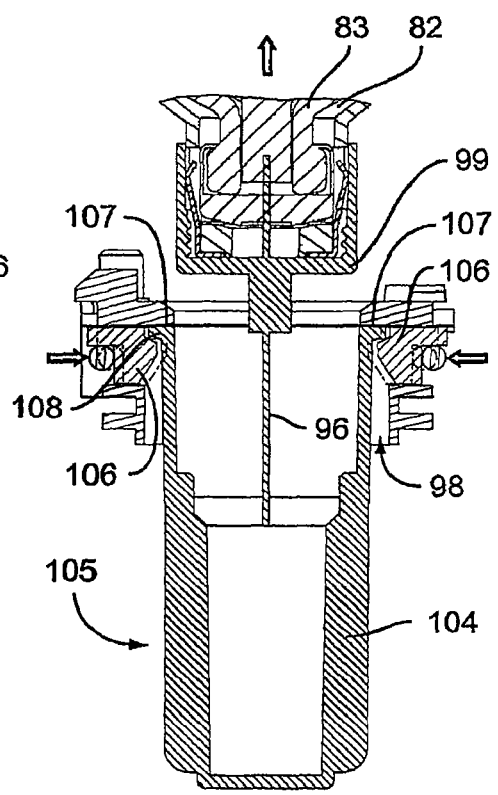

Fig.24
Fig.25
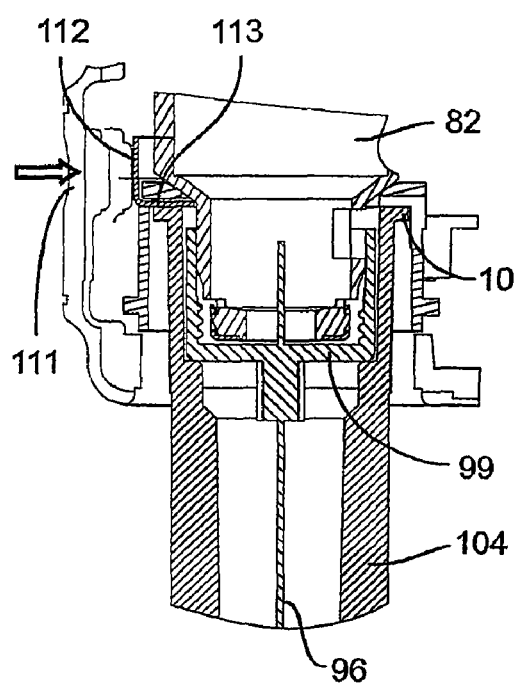
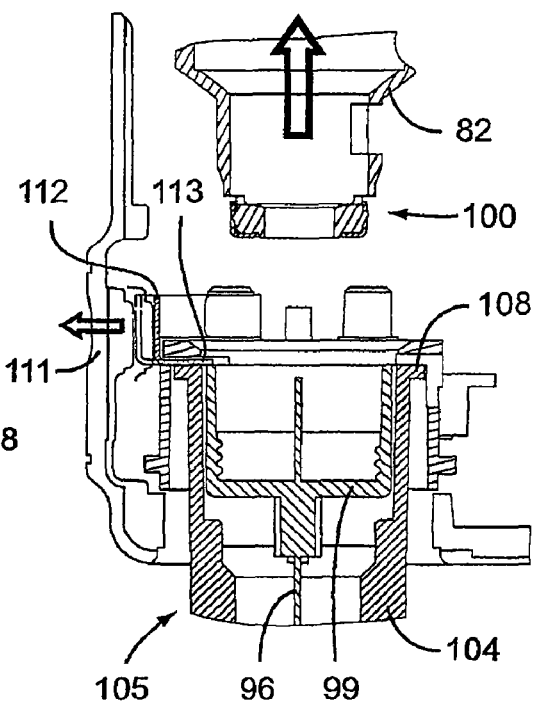

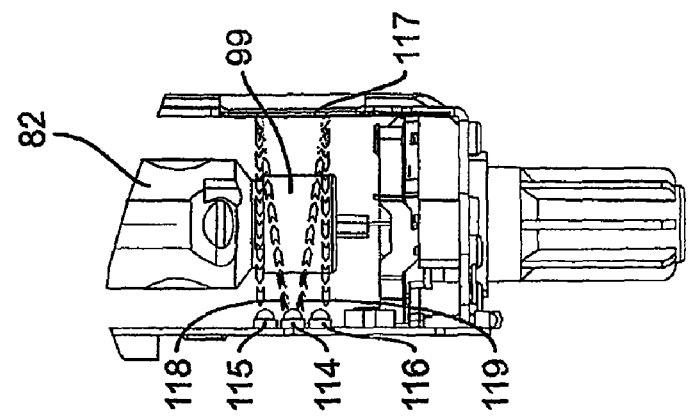
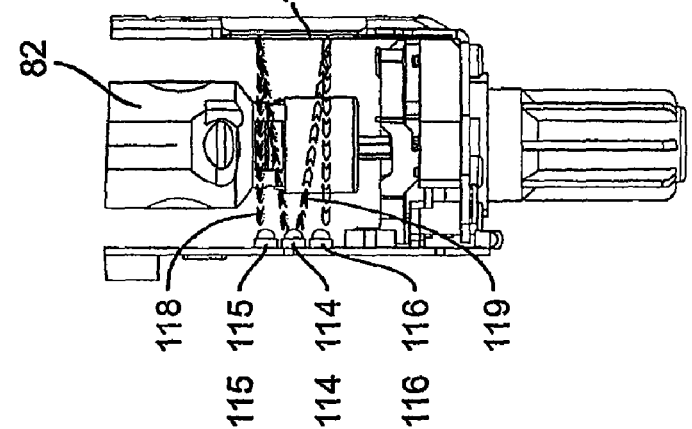
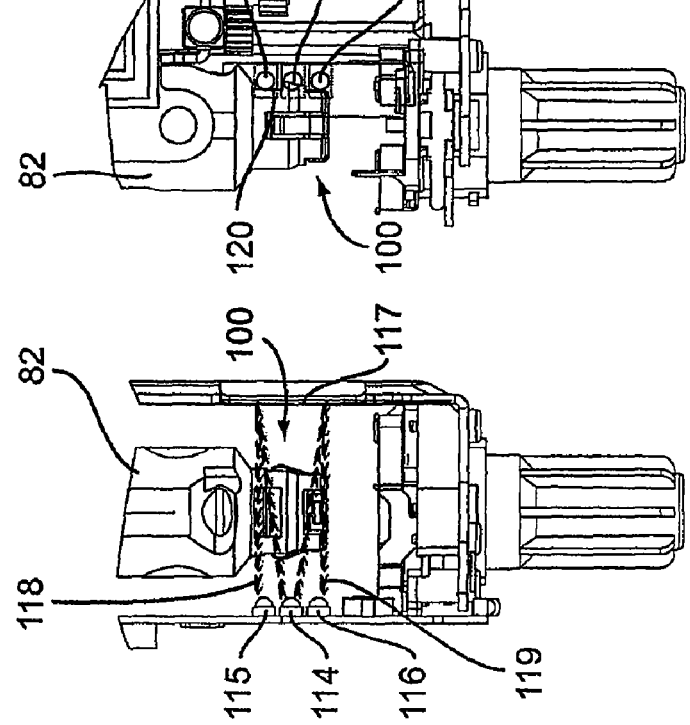

HAND-HELD ELECTRONICALLY CONTROLLED INJECTION DEVICE FOR INJECTING LIQUID MEDICATIONS

CROSS-REFERENCE TO RELATED APPLICATION

This application is a continuation of co-pending U.S. application Ser. No. 12/717,344, filed Mar. 4, 2010 which is a continuation of U.S. application Ser. No. 10/589,465, filed Oct. 16, 2006, now U.S. Pat. No. 7,704,231 which is a national stage application of International Application No. PCT/EP2005/050711, entitled, "Hand-Held Electronically Controlled Injection Device For Injecting Liquid Medications Technical Field", which was filed on Feb. 17, 2005 and which claims priority of European Patent Application No. 04100647.9, filed Feb. 18, 2004, the contents of each are herein incorporated by reference in its entirety.

TECHNICAL FIELD

The present invention relates to a hand-held, electronically controlled injection device for injecting liquid medications, and in particular of the type for performing subcutaneous injections fully automatically.

BACKGROUND ART

As is known, certain types of diseases, such as diabetes, call for injecting medications, such as insulin, several times a day, and the medication dosage to be injected may vary from one patient to another, and, for the same patient, during the day and from one day to another.

Over the past few years, therefore, electronically controlled injection devices have been devised and widely used to permit self-injection of medications in the required doses.

Patent Application US-A-2002/0133113 describes one such injection device substantially comprising a hand-held housing, which houses a cartridge containing the liquid medication for injection, and defines, on a contact surface for contacting the patient's skin, a through opening by which to fit a disposable needle to one end of the cartridge. The injection device also comprises an electromechanical actuator assembly, which is activated selectively to slide a plunger hermetically inside the cartridge body and deliver the liquid medication through the needle into the patient's skin.

Operation of the injection device is controlled by a programmable microprocessor, which receives signals from various switches and buttons—e.g. one or more medication dose selection buttons and an injection start button—and generates signals by which to control the actuator assembly according to a program stored in the microprocessor.

The injection device described therefore provides for selecting each medication dose for injection, and delivering the dose automatically.

Though functionally valid, the above type of injection device still leaves room for further improvement. More specifically, a need is felt for solutions designed to further reduce the amount of human intervention required, and to further safeguard users, with no medical experience, in preparing and self-injecting medications.

DISCLOSURE OF INVENTION

It is an object of the present invention to provide an electronically controlled injection device for injecting liquid medications, designed to meet the above requirement, and which in particular provides for preparing and performing subcutaneous injections fully automatically.

In an aspect, a medication delivery device comprises a housing, a door which, in an open position, permits insertion/removal of a medication container into/from the housing; a door opening mechanism for opening/closing the door; and a push member which can be moved axially from a retracted position, located outside the medication container, to enter said medication container and push liquid medication contained in said medication container out of the medication container to deliver it to a patient, and then return to its retracted position, the push member further comprising: a lock mechanism for locking at least part of the door opening mechanism to prevent opening of the door, when the push member is inside the medication container and for unlocking the door opening mechanism when the push member is in its retracted position.

BRIEF DESCRIPTION OF THE DRAWINGS

A preferred, non-limiting embodiment of the present invention will be described by way of example with reference to the accompanying drawings, in which:

FIGS. 4-8 show a portion of the FIG. 1 injection device illustrating assembly of a disposable needle;

FIGS. 9-11 illustrate removal of the needle from the injection device according to the first embodiment of the invention;

FIGS. 19-22 are section views showing a process of connecting the needle to the cartridge;

FIGS. 23-25 are section views showing a process of disconnecting the needle from the cartridge;

FIGS. 26-29 show an interior portion of the injection device according to the second embodiment, including sensor means for sensing connection of a needle to a cartridge;

BEST MODE FOR CARRYING OUT THE INVENTION

Figure 1:
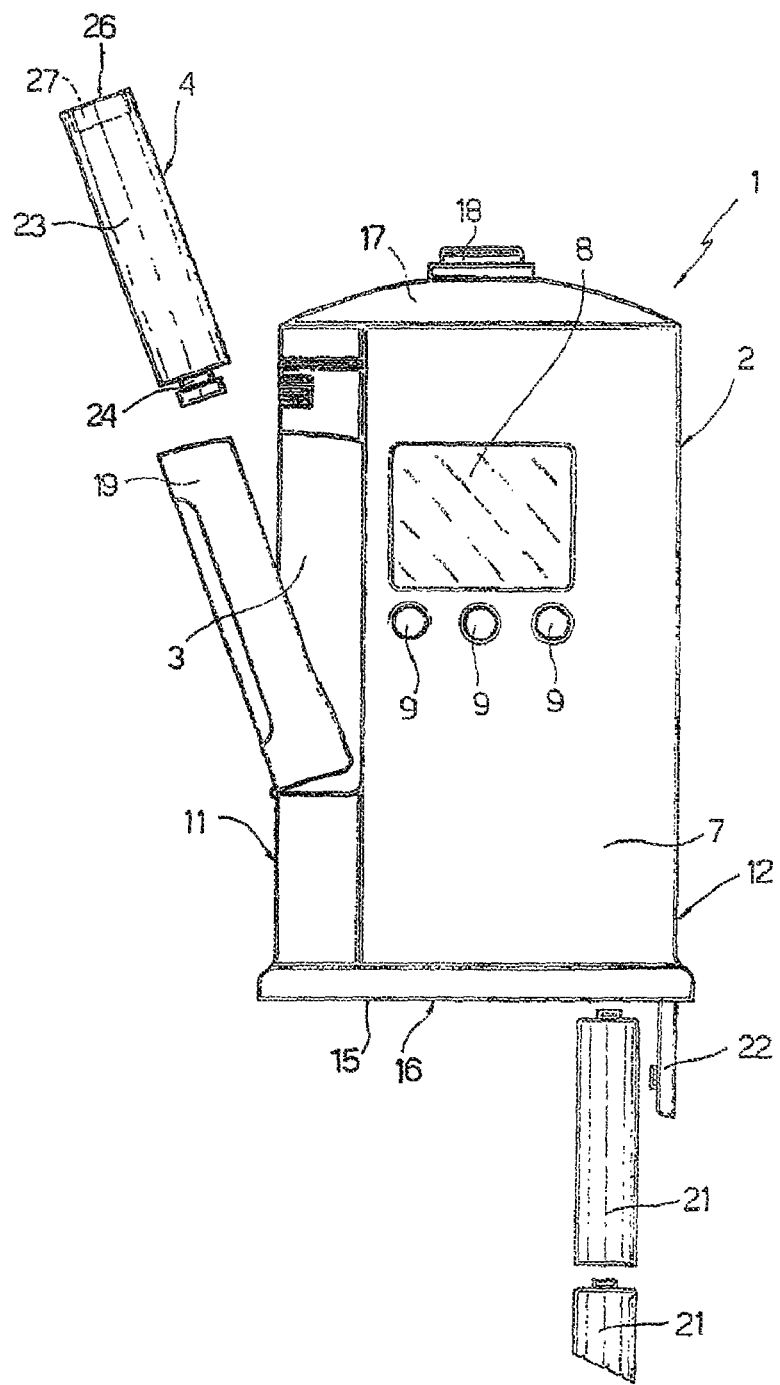
FIG. 1 shows a front view of an injection device in accordance with a first embodiment of the present invention.

Reference numeral 1 in FIG. 1 indicates as a whole a hand-held, electronically controlled injection device for injecting liquid medications, and in particular for performing subcutaneous injections fully automatically.

Injection device 1 substantially comprises a hand-held housing 2 defining a seat 3 for receiving a cartridge 4 containing the liquid medication; an injection driving unit 5 (FIGS. 2 and 3) housed inside housing 2 and selectively activated to cooperate with cartridge 4 and inject the patient with a preset dose of medication; and an electronic control unit 6 (FIG. 12) in the example shown, a microprocessor—also housed inside housing 2 to control operation of the injection driving unit 5.

More specifically, housing 2, in the example shown, is of thin prismatic shape, and comprises a front wall 7 fitted with an LCD display 8 and set-up buttons 9 (operation of which is described in detail later on); a rear wall 10; two sides 11,12; a bottom wall 15 defining a contact surface 16 for contacting the patient's skin; and a top wall 17 fitted with an injection start button 18, as explained in detail below.

As shown in FIG. 1, one of the sides 11 of housing 2 has a door 19 hinged at the bottom about an axis perpendicular to a front wall 7 and a rear wall 10, and which opens outwards to permit insertion of cartridge 4 inside the seat 3.

In the example shown, seat 3 is for receiving cartridge 4 has an axis A perpendicular to bottom wall 15 and top wall 17, and is formed close to side 11.

Close to the opposite side 12, housing 2 also defines a seat 20 (FIGS. 1 to 3) having an axis parallel to axis A, and for receiving one or more batteries 21 for electrically powering injection device 1, and which are inserted through a further door 22 formed in bottom wall 15.

As shown in FIGS. 1 to 11, the cartridge 4 is defined by a hollow cylindrical body 23 containing a predetermined quantity of liquid medication, and having a closed, small-section end 24, through which a commonly marketed disposable needle 25 is insertable in known manner, and an open opposite end 26 engaged in fluidtight manner by a disk-shaped member or plunger 27, which is activated by injection driving unit 5 to slide inside body 23 and deliver the medication through needle 25.

Cartridge 4 is inserted inside housing 2 with end 24 for needle 25 facing bottom wall 15 and, therefore, the contact surface 16 for contacting the patient's skin; and bottom wall 15 has a through opening 30, of axis A, by which to fit and remove the needle 25 to/from the cartridge 4, and through which the needle 25 is ejected to inject the skin.

Cartridge 4 has known external markings (not shown), e.g. bar codes, <BR> <BR> notches, conducting or reflecting material in a predetermined pattern, etc., by which to determine the presence of the cartridge 4 inside the housing 2, and to obtain information relating to the medication, such as composition, concentration, expiry date, etc. Another possibility for identifying the cartridge 4 is to use a radio frequency identification system.

As shown clearly in FIGS. 4 to 6, the needle 25 is supplied in a protective needle housing 31 to prevent injury to the user, and defines, with the needle housing 31, a needle assembly 32.

More specifically, the needle 25 is fixed to and projects from a plastic needle support 33 which fits onto an end 24 of the body 23 of cartridge 4.

As is known, the needle 25 comprises a front portion 34 (at the bottom in FIGS. 2 to 11) for piercing the patient's skin and which projects from the needle support 33; and a rear end 35 (at the top in FIGS. 4 to 11) enclosed in the needle support 33 and which fits through end 24 of the body 23 of the cartridge 4. More specifically, the needle support 33 comprises a number of elastic flanges 36 surrounding the rear end 35 of the needle 25, and which engage the end 24 of the body 23 of the cartridge 4 as described in detail below.

As an alternative not shown, the reverse arrangement of the engagement between the needle support and the cartridge end is also possible. In this latter case, the cartridge end may be provided with elastic flanges engaging the needle support. This further embodiment has the advantage that the needle support need not be specially designed with elastic flanges, but rather a standard commercially available needle assembly may be used (even one with screw threads, which is a common commercially available version).

Needle housing 31 is defined by a cylindrical, cup-shaped body housing the front portion 34 of the needle 25, and the open end of which is fitted to the needle support 33. In the example shown, the needle assembly 32 also comprises an inner needle housing 37 covering the front portion 34 of the needle 25.

Figure 2:
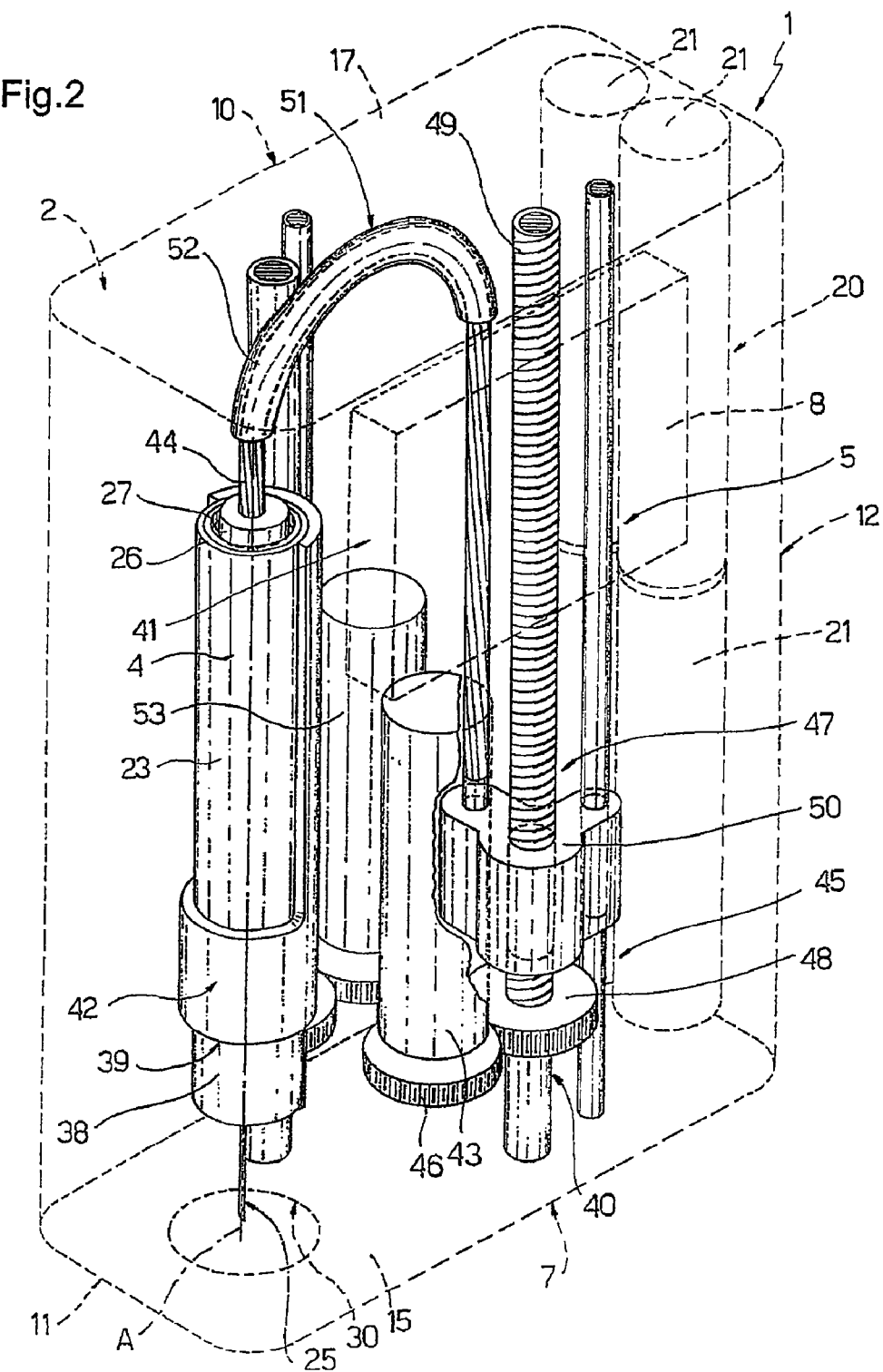
FIGS. 2 and 3 show, with parts removed for clarity, larger-scale views in perspective, from opposite sides, of the internal components of the FIG. 1 injection device.
Figure 3:
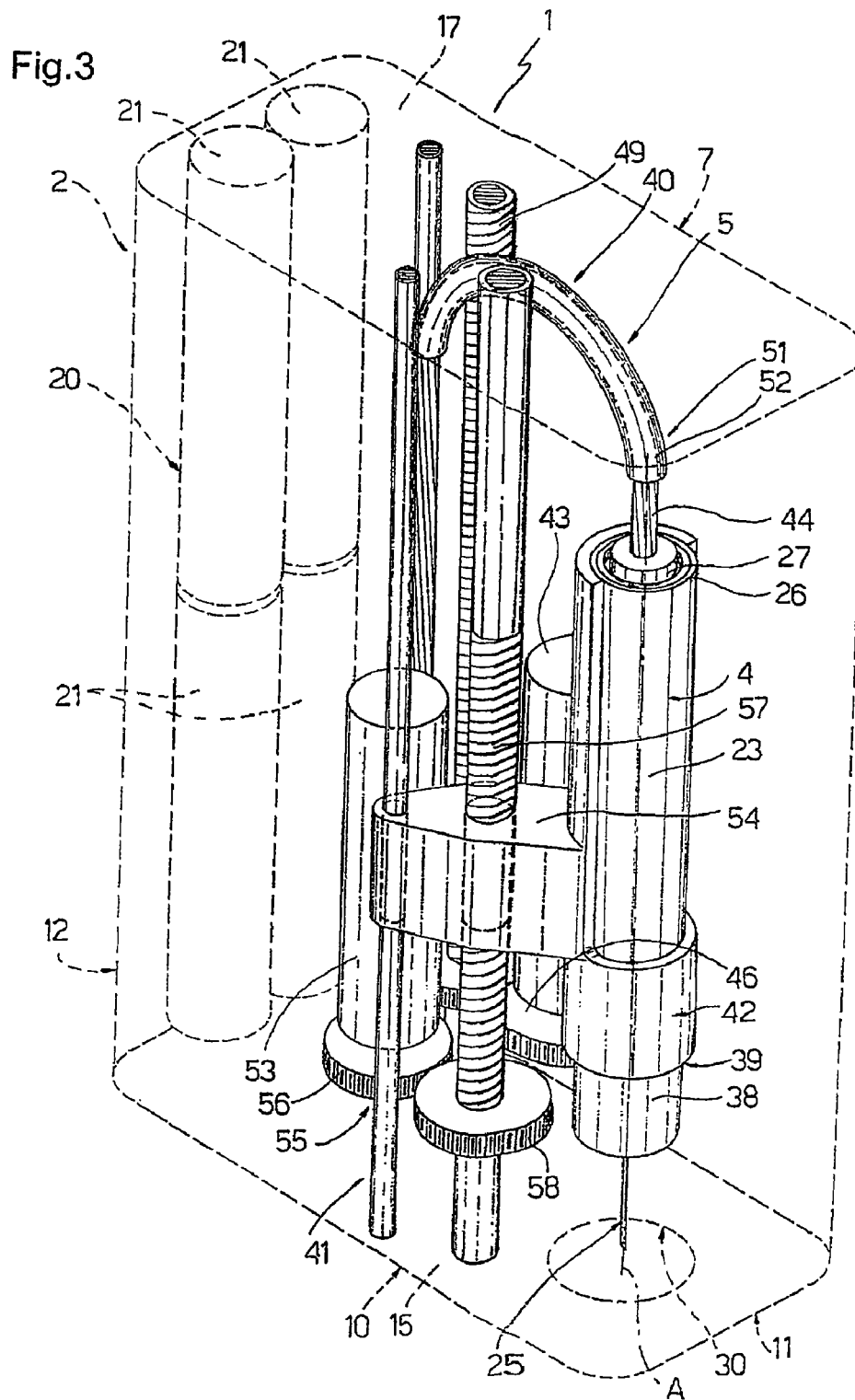

With reference to FIGS. 2 and 3, the injection driving unit 5 comprises an electromechanical actuator assembly 40, which is selectively activated to act on the plunger 27 of the cartridge 4 and move it, inside the body 23 of the cartridge 4, towards the end 24 to deliver the liquid medication through the needle 25.

According to an important aspect of the present invention, the injection driving unit 5 comprises a further electromechanical actuator assembly 41 for moving the cartridge 4, inside housing 2 and along axis A, to and from the contact surface 16 to automatically fit and remove needle 25 to/from cartridge 4, and to insert the needle 25 inside the patient's skin at a predetermined speed.

More specifically, the cartridge 4 is fitted to a supporting sleeve 42 which slides axially inside the seat 3 of the housing 2.

As shown in FIGS. 2 and 3, the supporting sleeve 42 is open, not only at opposite axial ends, but also on the side facing door 19 to permit insertion of the cartridge 4.

More specifically, the supporting sleeve 42 comprises a small-section bottom end portion 38 for receiving the end 24 of the cartridge 4, and which, when fitting needle 25 to cartridge 4, is engaged by the elastic flanges 36 of the needle support 33. End portion 38 also defines an annular shoulder 39 with the rest of the supporting sleeve 42.

Actuator assembly 40 comprises an electric gear motor 43; a push member 44 which acts on the plunger 27 of the cartridge 4 to move it, inside body 23 of the cartridge 4, towards end 24; and a transmission 45 for converting the rotation generated by the gear motor 43 into translation of the push member 44.

More specifically (FIG. 2), the transmission 45 substantially comprises a pinion 46 fitted to the output member of the gear motor 43; a screw assembly 47 connected to the push member 44; and an intermediate gear 48 having external teeth meshing with the pinion 46, and internal teeth engaging a leadscrew 49 of the screw assembly 47.

More specifically, the leadscrew 49 is fitted to the housing 2 to rotate but not translate axially. The screw assembly 47 also comprises a nut screw 50 fitted to the leadscrew 49, integral with the push member 44, and fitted to the housing 2 to translate along, but not rotate with respect to, the leadscrew 49.

Push member 44 is advantageously defined by the core of a known Bowden-type flexible cable 51, the sheath 52 of which has a portion fixed to housing 2, e.g. to the top wall 17.

Actuator assembly 41 comprises an electric gear motor 53; a slide 54 integral with supporting sleeve 42 of the cartridge 4 and movable parallel to axis A; and a transmission 55 for converting the rotation generated by the gear motor 53 into the translation of the slide 54.

More specifically (FIG. 3), the slide 54 is defined by a nut screw projecting laterally from the supporting sleeve 42 and fitted to the housing 2 to translate along, but not rotate with respect to, an axis parallel to axis A. Transmission 55 comprises a pinion 56 fitted to the output member of the gear motor 53; a leadscrew 57 connected to slide 54 and fitted to housing 2 to rotate about, but not translate along, its own axis; and an intermediate gear 58 having external teeth meshing with the pinion 56, and internal teeth engaging the leadscrew 57.

With reference to FIGS. 4 to 11, the injection device 1 also comprises two or more retaining elements 60 extending about the seat 3 to keep the needle assembly 32 fitted to housing 2 in a predetermined position (FIG. 5). The assembly 32 projects along axis A from bottom wall 15 of the housing 2, and the portion having the needle support 33 engages the opening 30 in wall 15.

More specifically, retaining elements 60 are defined by levers extending parallel to axis A and having top ends 61 hinged to a structural portion of the housing 2, and free bottom ends having locking flanges 62. More specifically, the locking flanges 62 are located at opening 30, and extend perpendicular to the axis A and inwards of the opening 30.

Retaining elements 60 are loaded elastically inwards of the seat 3 to assume a lock configuration (FIGS. 5, 6, 10 and 11), and are parted into a release configuration (FIGS. 4, 7, 8 and 9) by the respective cam profiles 63 interacting with a contoured annular projection 64 on the supporting sleeve 42, as the supporting sleeve 42 moves along axis A.

More specifically, the supporting sleeve 42 and, with it, the cartridge 4 are movable jointly by the actuator assembly 41 in opposite directions along axis A to assume three distinct positions, namely:
  a top limit position (FIGS. 4 and 7) in which the cartridge 4 is loaded and any automatic operation of the injection device 1 (in this case, assembling and removing needle 25, and injecting the patient with medication) starts and ends;
  a bottom limit position (FIGS. 10 and 11) in which the needle 25 is removed from the cartridge 4; and
  an operating position (FIG. 6), close to the bottom limit position, in which the liquid medication is delivered through the patient's skin, and the needle 25 is connected to the cartridge 4.

As shown in FIGS. 4-11, the cam profile 63 of each retaining element 60 and the projection 64 on the sleeve support 42 are in the form of complementary ramps and designed to cooperate mutually to part the retaining elements 60 in and close to the top limit position of the supporting sleeve 42, and to detach from each other, leaving the retaining elements 60 subjected solely to the elastic return force towards axis A, in the other positions assumed by the supporting sleeve 42 during its movement.

As shown in FIGS. 5 and 6, in the lock configuration, the locking flanges 62 of retaining elements 60 cooperate with an outer rib 65, formed at the open end of the needle housing 31, to retain the needle assembly 32 inside the opening 30 in the bottom wall 15 as the supporting sleeve 42 moves into the operating position, so that the end portion 38 of the supporting sleeve 42 fits inside the elastic flanges of the needle support 33, and the rear end 35 of needle 25 is inserted inside the end 24 of the cartridge 4.

As the supporting sleeve 42 moves subsequently from the operating position to the top limit position, the locking flanges 62 of the retaining elements 60, still in the lock configuration, press on the needle housing 31 to prevent it following the needle 25, the needle support 33 and the inner needle housing 37 moving together with the supporting sleeve 42, so that the needle 25 and the needle support 33 can be connected to the cartridge 4 and withdrawn from the needle housing 31 automatically.

One will note that the retaining elements 60, as they press on the needle housing 31, and lock the needle housing 31 with respect to the user too. Thus, untimely removal of the needle housing 31 by the user, e.g. as the needle 25 is being connected to the cartridge 4, is prevented.

In the bottom limit position of the supporting sleeve 42 (FIGS. 10 and 11), the locking flanges 62 of the retaining elements 60 engage the gap between the shoulder 39 of the supporting sleeve 42 and the rear end of the needle support 33 to arrest the needle support 33 as the supporting sleeve 42 subsequently moves into the top limit position, so that the needle 25 and the needle support 33 are withdrawn automatically from the cartridge 4 after use.

Figure 12:
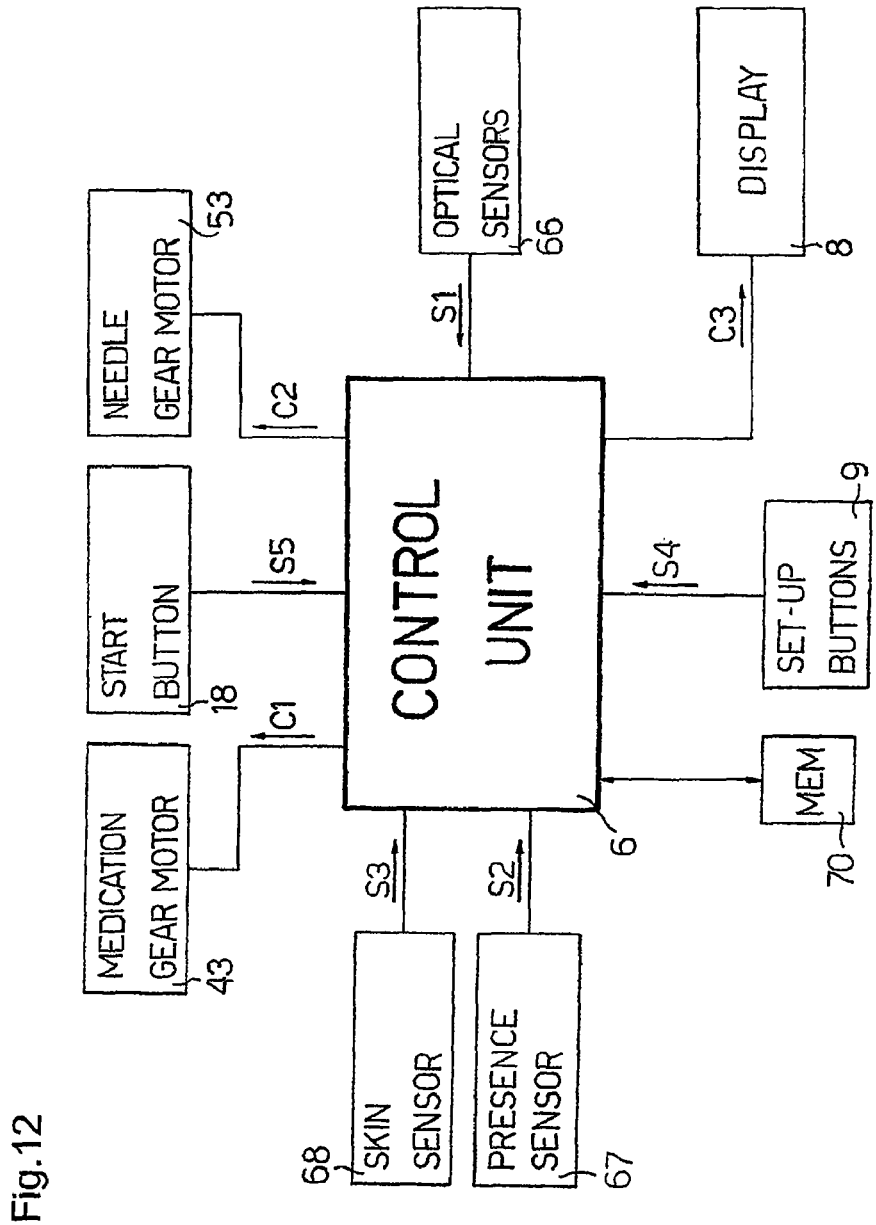
FIG. 12 shows a block diagram illustrating operation of a control unit for controlling the FIG. 1 injection device.
Figure 13:
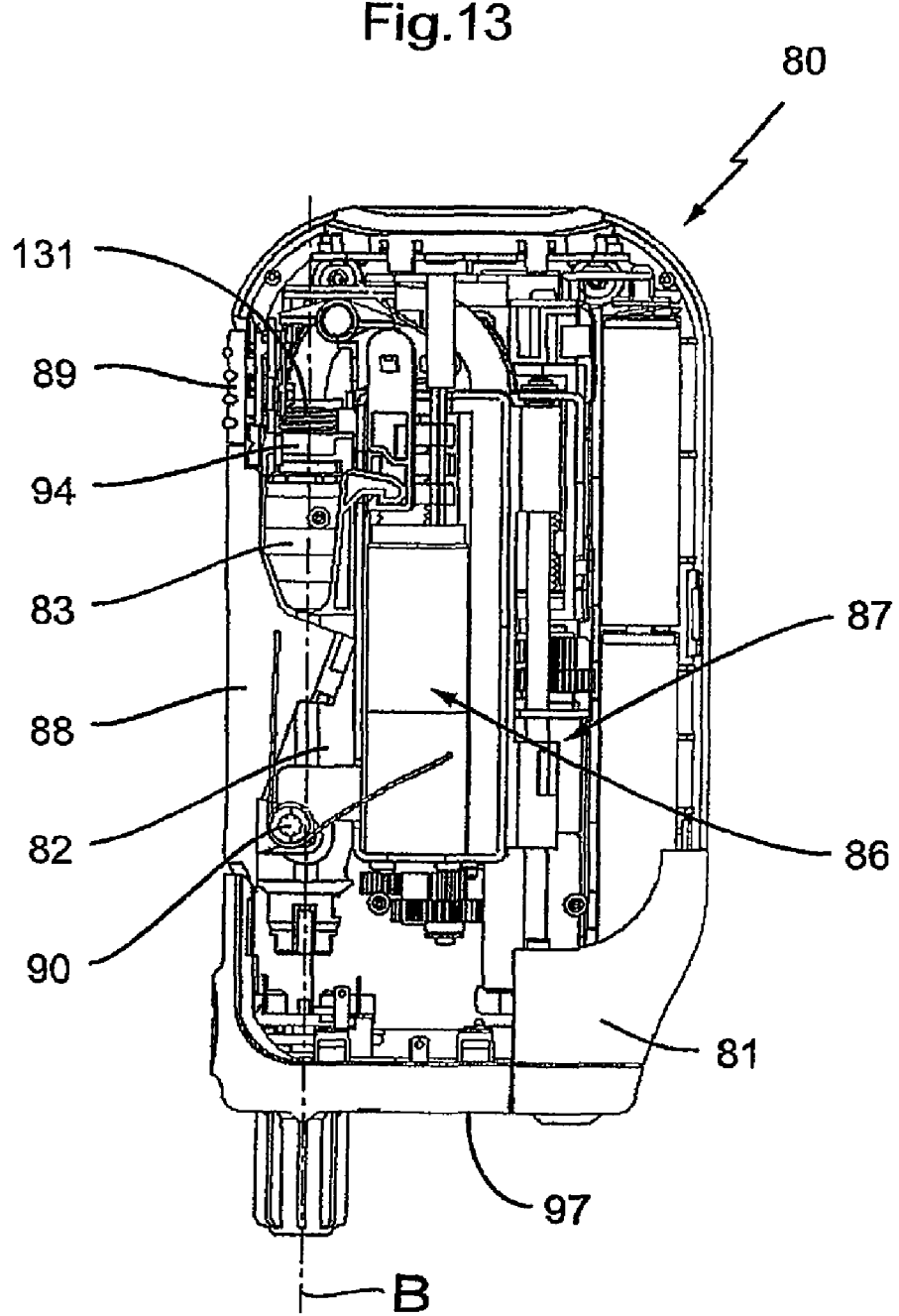
FIGS. 13 and 14 are front views of an injection device according to a second embodiment of the invention, with a front wall removed to show the interior of the device.
Figure 14:
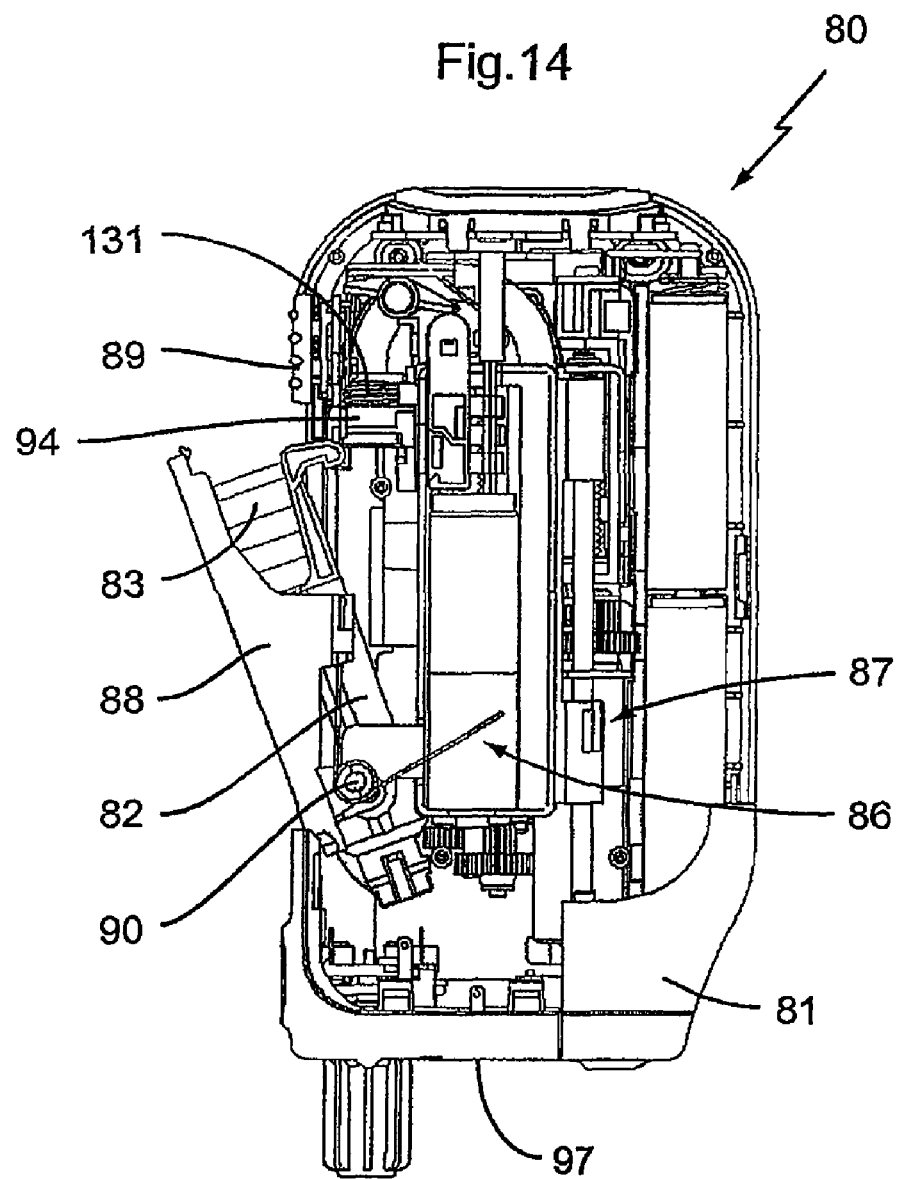

With reference to FIG. 12, the control unit 6 receives a number of signals from various detecting elements and buttons on the injection device 1, and supplies control signals for the gear motors 43, 53 and the display 8, according to a program stored in the control unit 6 itself.

More specifically, the control unit 6 receives the following signals:
  signals S1 from the sensors 66 (e.g. optical, electrical, radio-frequency, infra-red, etc.) facing the seat 3 and for detecting the markings on the cartridge 4;
  a signal S2 from a presence sensor 67, e.g. a contact switch, located at the opening 30 in the bottom wall 15 and for determining engagement of the opening by an outer body of predetermined diameter, e.g. the needle housing 31;
  a signal S3 from a skin sensor 68, e.g. a mechanical or capacitive sensor, located on the bottom wall 15 of the housing 2 and for determining contact with the patient's skin;
  signals S4 from the set-up buttons 9, by which to select, for example, the dose for injection, the speed at which the needle 25 penetrates the patient's skin, medication delivery speed, etc; and
  a signal S5 from the injection start button 18.

On the basis of the incoming signals, the control unit 6 supplies signals C1 and C2 for controlling the respective gear motors 43, 53 in both rotation directions, and a signal C3 for controlling the display 8.

Control unit 6 has its own internal memory 70 (shown externally for the sake of simplicity) which stores the action program of the control unit 6 and the doses and timing of the injections performed, so as to inform the patient and/or doctor of these and the number of doses left in the cartridge 4. The doctor can therefore check patient compliance.

Injection device 1 is also provided with an interface (known per se and not shown), e.g. a USB port, a Bluetooth communication, an infra-red port, etc., that allows for information exchange with a computer for data analysis.

Programming of the injection device 1 may also be possible (for example by uploading from a computer), which may be useful for clinic trials (for example, permitting injection only of certain amounts and at certain times/intervals).

Operation of the injection device 1 will be described in regards to the FIG. 4 configuration, in which the supporting sleeve 42 has no needle 25 and is set to the top limit position, and the cartridge 4 has been inserted through the door 19 into the seat 3 of the housing 2 and connected to the supporting sleeve 42.

Assembly of the needle 25 to the cartridge 4 is controlled fully automatically by the control unit 6, and is activated by simply inserting the needle assembly 32, by the open end of the needle housing 31, inside the opening 30 in the bottom wall 15 of the housing 2. Insertion of the needle assembly is immediately detected by the presence sensor 67, so that the control unit 6 activates the gear motor 53 in the direction designed, via the transmission 55 and the slide 54, to move the supporting sleeve 42 into the operating position.

As a result of the above movement of the supporting sleeve 42, the projection 64 is detached from the cam profiles 63, so that the retaining elements 60 move inwards of the opening 30, and the locking flanges 62 close onto the needle housing 31 to lock it in position partly engaging the opening 30 (FIG. 5).

Needle assembly 32 can be inserted inside the opening 30 either by hand or using an adapter indicated as a whole by 71 in FIGS. 4-10.

More specifically, the adapter 71 is double-cup-shaped, and comprises opposite portions 72,73 of different diameters defining respective cavities open on opposite sides and for housing the needle housing 31 and the inner needle housing 37 respectively. The larger-section portion 72 also houses a cylindrical slip sleeve 76 defining the actual seat for the needle housing 31, and the function of which is explained later on; and the smaller-section portion 73 is provided internally, dose to the open end, with an inner rib 74 which presses on the inner needle housing 37 to remove it from the assembly defined by the needle 25 and the needle support 33.

As the supporting sleeve 42 reaches the operating position (FIG. 6), the end portion 38 is inserted between the elastic flanges 36 and connected to the needle support 33, and the rear end 35 of the needle 25 is inserted inside the end 24 of the cartridge 4.

At this point, the rotation direction of the gear motor 53 is inverted, and the supporting sleeve 42 moves from the operating position to the top limit position. As it does so, the needle support 33, the needle 25 and, with it, the inner needle housing 37 are withdrawn axially from the needle housing 31 locked partly engaging the opening 30 by the retaining elements 60.

Close to the top limit position, the projection 64 on the supporting sleeve 42 interacts with the cam profiles 63 of the retaining elements 60 to part the retaining elements 60, so that the locking flanges 62 move outwards of the opening 30 to release the needle housing 31 (FIG. 7).

Once supporting sleeve 42 reaches the top limit position, the adapter 71 can be inserted through the opening 30 into the seat 3 by the portion 73, the cavity of which is thus engaged by the inner needle housing 37. Given its smaller diameter, insertion of the portion 73 is not detected by presence the sensor 67. When the adapter 71 is extracted from the opening 30, the inner needle housing 37 is removed from the needle 25 (FIG. 8).

Consent to start the actual injection is given by the surface 16 contacting the patient's skin and so activating the skin sensor 68.

When the start button 18 is pressed, the gear motor 53 is first activated and, via the transmission 55, moves the supporting sleeve 42 back into the operating position, so that the needle 25 penetrates the patient's skin. Gear motor 43 is then activated and, via the transmission 45 and the push member 44, acts on the plunger 27 of the cartridge 4 to slide it towards the end 24 and deliver a predetermined dose of liquid medication.

Before the injection is performed, the dose to be injected, the speed at which needle 25 penetrates the patient's skin, the speed at which the liquid medication is delivered and the injection depth can be selected using the set-up buttons 9 and displayed on the display 8. Once the injection is completed, the supporting sleeve 42 moves back into the top limit position.

The needle 25 can be removed from the cartridge 4 fully automatically using the adapter 71 (FIGS. 9 and 10), or directly using a needle box 75 (FIG. 11), e.g. of the type known by the trade name "SHARPS BOX". More specifically, when using the adapter 71 in removing the needle housing 31 and the inner needle housing 37 (FIGS. 9 and 10), the slip sleeve 76 is first extracted from the portion 72 to rest axially on the rib 65 of the needle housing 31.

At this point, the needle housing 31 and the extracted part of slip sleeve 76 are inserted through the opening 30 in the housing 2 to activate the presence sensor 67, so that the control unit 6 activates the gear motor 53 to move the supporting sleeve 42 from the top limit position to the bottom limit position.

As the cam profiles 63 are detached from the projection 64 on the supporting sleeve 42, the retaining elements 60 are prevented from moving into the lock configuration by the locking flanges 62 resting on the slip sleeve 76 of the adapter 71 (FIG. 9).

As the supporting sleeve 42 reaches the bottom limit position (FIG. 10), however, the locking flanges 62 of the retaining elements 60 click inside the gap between the shoulder 39 on the supporting sleeve 42 and the top axial end of the needle support 33.

At this point, the rotation direction of the gear motor 53 is inverted, and the supporting sleeve 42 moves into the top limit position. As it does so, the needle support 33 and the needle 25 remain in the position in which they are retained by the locking flanges 62, and are thus withdrawn axially from the supporting sleeve 42 and the cartridge 4.

As the supporting sleeve 42 reaches the top limit position, the retaining elements 60 are again parted, and the injection device 1 is ready to be fitted with another needle 25 for the next injection.

When using the needle box 75 (FIG. 11), this is simply inserted by the mouth end inside the opening 30 to activate the presence sensor 67 and automatically remove the needle 25 from the cartridge 4 in exactly the same way as described relative to the adapter 71.

The advantages of the injection device 1 according to the present invention will be clear from the foregoing description. In particular, by permitting control of the movement of the cartridge 4 to and from the contact surface 16, the injection device 1 provides for fully automatically fitting and removing the needle 25 to/from the cartridge 4, and controlling the speed at which the needle 25 penetrates the patient's skin.

In other words, when the actual injection is performed, it is possible to set not only the medication dose and the speed at which the dose is delivered, but also the speed at which the needle 25 is ejected from the housing 2, and therefore skin penetration speed.

Clearly, changes may be made to the injection device 1 as described and illustrated herein without, however, departing from the scope of the accompanying Claims.

In particular, the movement of the cartridge 4 and delivery of the medication contained in the cartridge 4 may be controlled using a single gear motor, which may, for example, by means of a transmission similar to those described, control axial displacement of the core of a Bowden-type flexible cable acting on the plunger 27 of the cartridge 4; and releasable locking means may be provided for selectively making the plunger 27 and the body 23 of the cartridge 4 integral with each other, so that, when the locking means are activated, the cartridge 4 is moved to and from the contact surface 16, and, when the locking means are released, the plunger 27 slides inside the body 23 of the cartridge 4 to deliver the medication. Furthermore, the injection device 1 can be used, in the same way as disclosed, with other types of medication containers, such as a syringe.

FIGS. 13-16 show a hand-held, electronically controlled injection device 80 according to a second embodiment of the invention. Like the injection device 1 according to the first embodiment, the injection device 80 shown in FIGS. 13-16 comprises, inside a housing 81 (shown in FIG. 13, 14 only), a cartridge holder 82 for accommodating a cartridge 83 containing a liquid medication, a push member 84 designed to act on a plunger 85 of the cartridge 83, a first electromechanical actuator assembly 86 for driving the push member 84 and a second electromechanical actuator assembly 87 for axially moving, in particular, the cartridge holder 82. A door 88 provided on a side wall of the housing 81, and actuated by a sliding button 89 provided on the same side wall, may be opened by being rotated about a pivot axis 90 to insert or remove a cartridge 83 into/from the injection device. Cartridge holder 82 is axially movable relative to the door 88 but rotatable with the door 88 about the pivot axis 90 when in an axial retracted position.

Push member 84 comprises an axially incompressible and laterally flexible tube 91, having the form of a spring, and deflected by 180° by a guiding rigid semi-circular housing 92 at an upper part of the device, and a piston 93 fixed to an end of tube 91 projecting from housing 92 along the axis B of the cartridge holder 82 and the cartridge 83. Piston 93 is designed to cooperate with the plunger 85 of the cartridge 83 (see FIG. 16) as well as with a movable recessed part 94 (see FIG. 15) the function of which will be described below.

Figure 15:
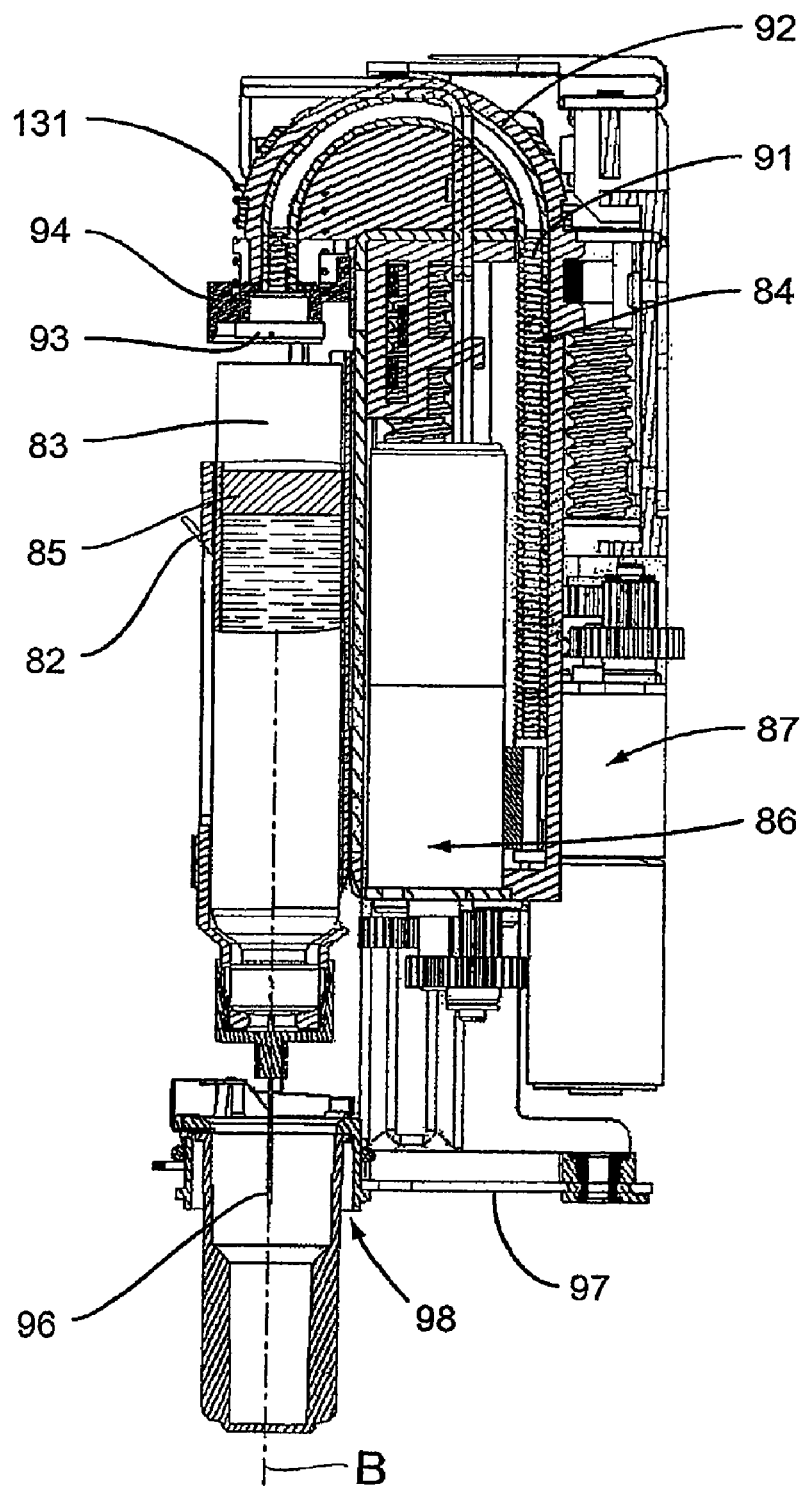
FIGS. 15 and 16 are section views of the interior of the injection device according to the second embodiment, showing two different positions of a push member of the device.
Figure 16:
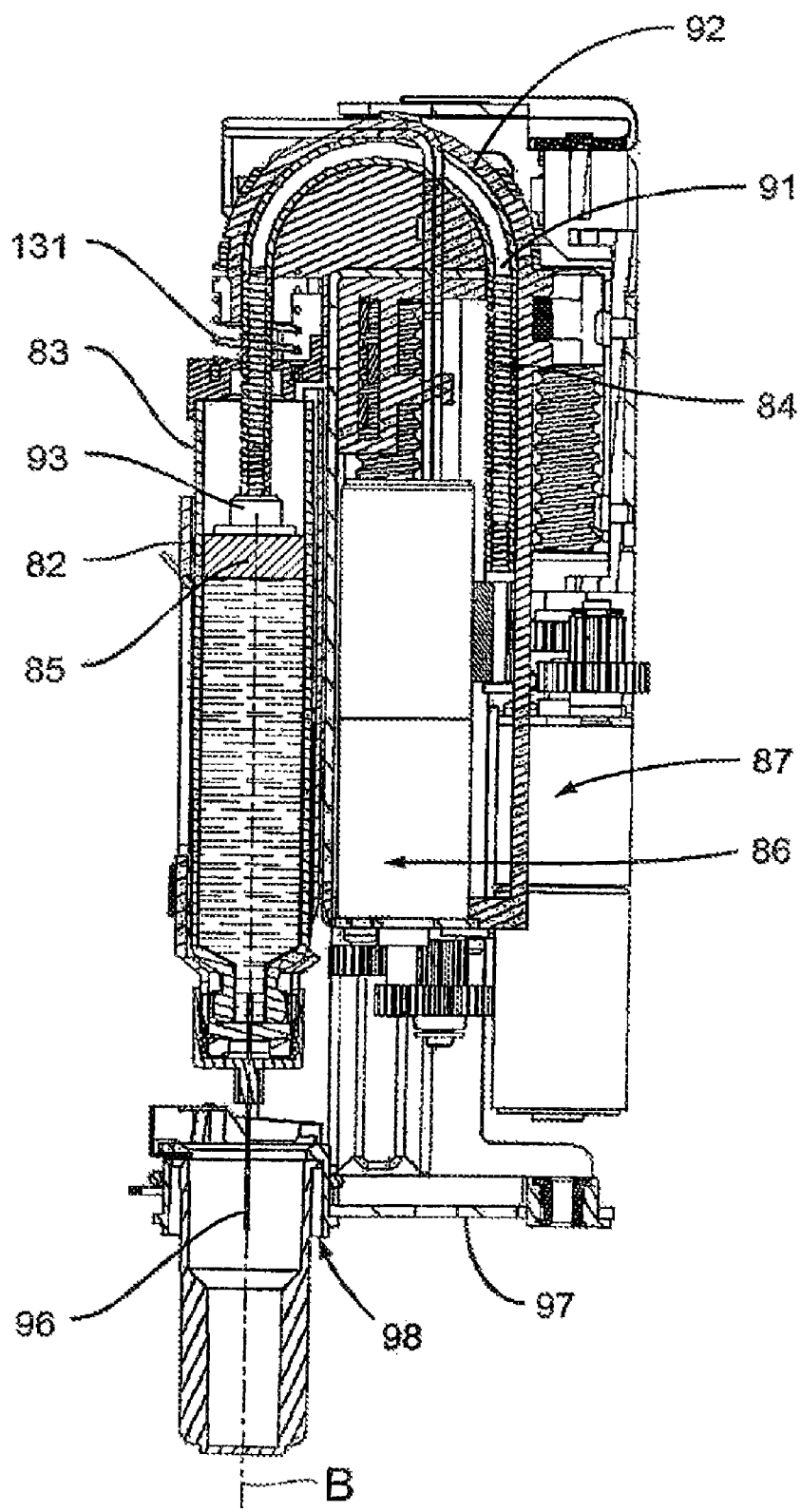
Figure 41:
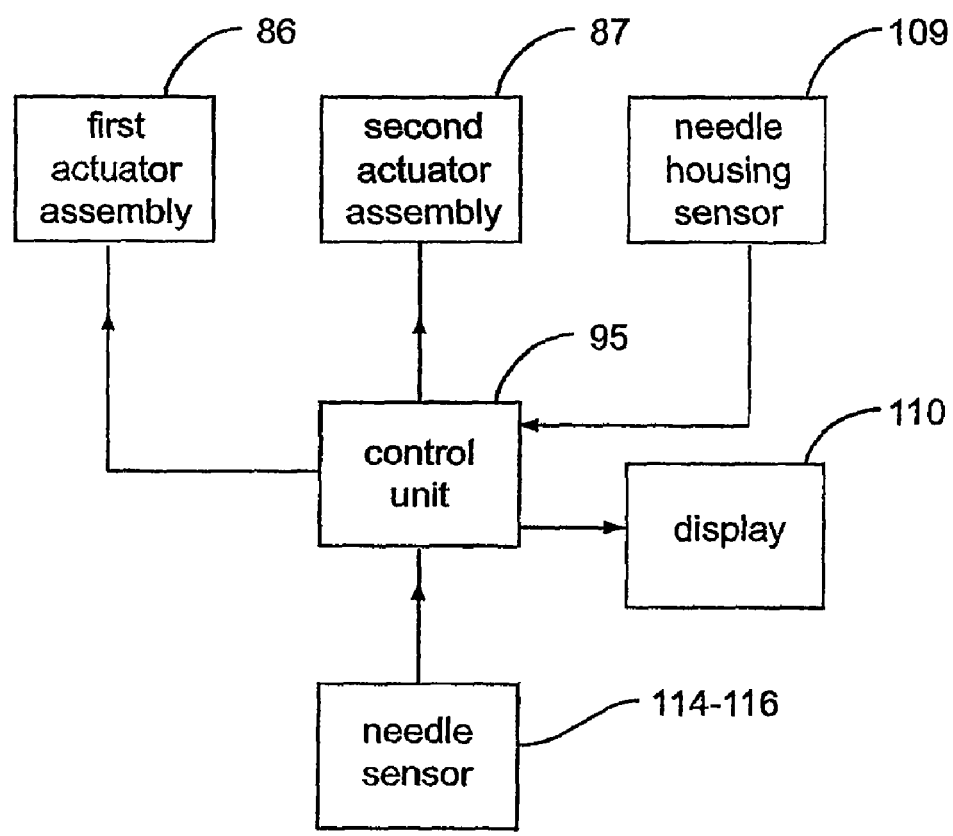
FIG. 41 is a block diagram illustrating operation of a control unit for controlling the injection device according to the second embodiment.

Under the control of a control unit 95, represented in FIG. 41, the first actuator assembly 86 may move the push member 84 axially from a retracted position, in which the piston 93 is outside the cartridge 83 and within the recessed part 94 (FIG. 15), towards a disposable needle 96 connected to the cartridge 83, so that the piston 93 comes into contact with the plunger 85 within the cartridge 83 and pushes the plunger 85 to deliver medication through the needle 96 (FIG. 16). Push member 84 may then be moved back to its retracted position, leaving the plunger 85 at the position it was pushed to.

Second actuator assembly 87 may be controlled by the control unit 95 to move a structure comprising the first actuator assembly 86, the push member 84, the push member housing 92 and the cartridge holder 82 along axis B, i.e. to and from a bottom wall 97 of device housing 81 for contact with the patient's skin, to automatically fit and remove needle 96 to/from cartridge 83 and to insert and remove needle 96 into/from the patient's skin. More precisely, the structure 82, 84, 86, 92 may be moved between a top, retracted position in which the needle 96 connected to the cartridge 83 is within the device housing 81, and one or more bottom positions in which the needle 96 projects from a through opening 98 provided in the bottom wall 97.

Figure 17:
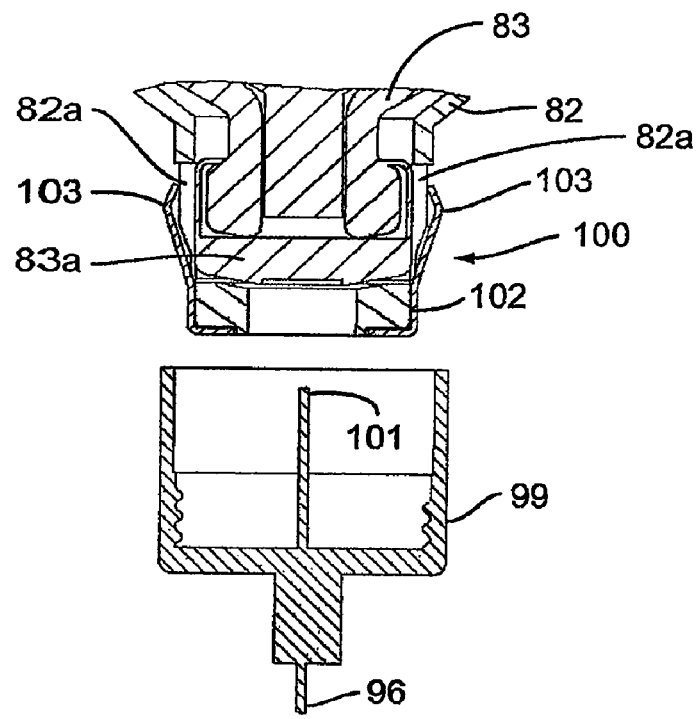
FIGS. 17 and 18 are section views showing a needle and an end of a cartridge inserted in the injection device according to the second embodiment, respectively in a disassembled state and in an assembled state.
Figure 18:
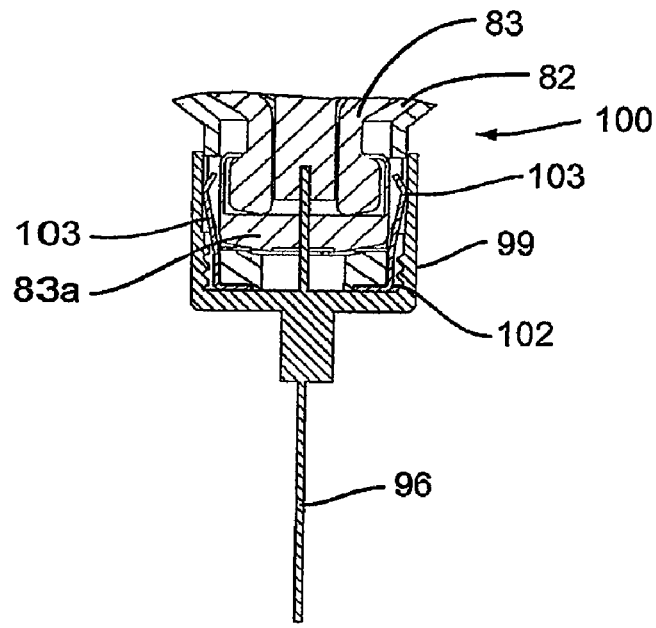

Referring to FIGS. 17 and 18, the needle 96 is fixed to and projects from a plastic needle support 99 which fits onto a bottom end 100 of the cartridge holder 82 so that the corresponding bottom end 83a of the cartridge 83, surrounded by the bottom end 100, is pierced by the rear end 101 of the needle 96. Fitting of the needle support 99 onto the cartridge holder 82 is achieved by means of an intermediate metal member 102 fixed to the bottom end 100 of the cartridge holder 82 and having a number of elastic flanges 103 which may be compressed between the external circumferential wall of the bottom end 83a of the cartridge 83 and the internal circumferential wall of the needle support 99 in the grooves 82a provided in the cartridge holder wall.

Figure 19:
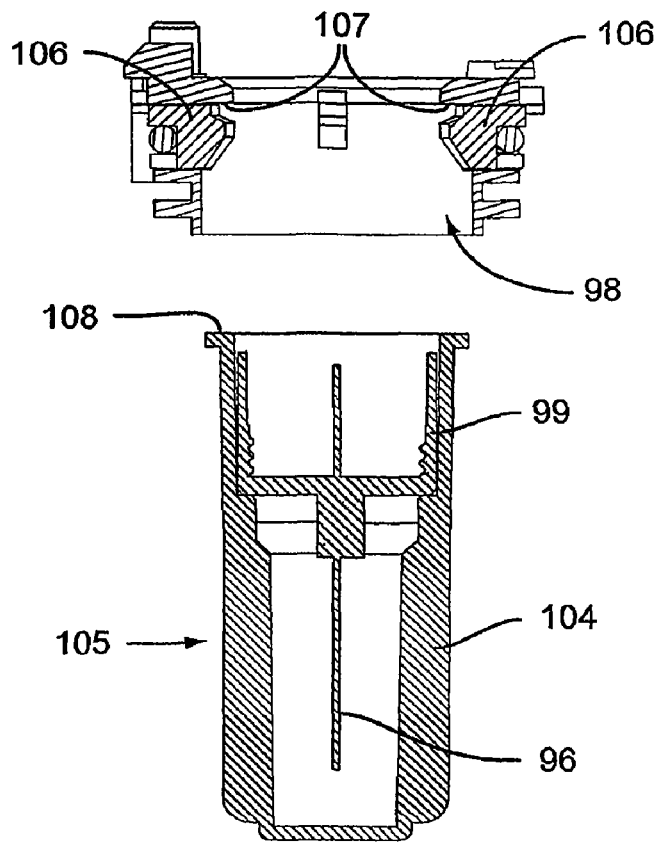
Figure 20:
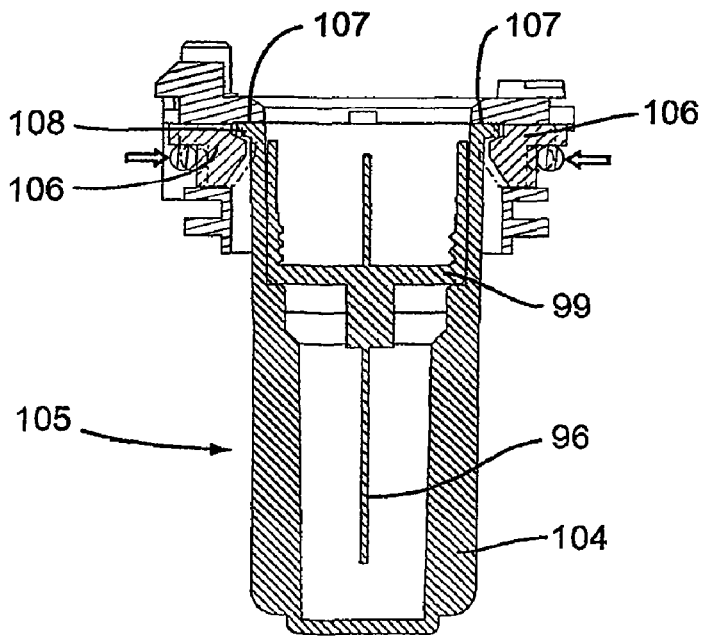

Before connection of the needle 96 to the cartridge 83, the needle support 99, with the needle 96, is fitted in a protective needle housing or needle cap 104 and forms with the latter a needle assembly 105 (see FIGS. 19-20). Referring to FIGS. 19-20, the injection device 80 according to this second embodiment further comprises releasable retaining means for retaining the needle assembly 105 in a predetermined position inside the opening 98 of the bottom wall 97. These releasable retaining means comprise two or more releasable retaining tabs or fingers 106, which are actuated by the needle assembly 105 upon its insertion into the opening 98, and an axial abutment surface 107 which limits insertion of the needle assembly 105 into the opening 98. Releasable retaining tabs 106 are disposed on the circumference of the opening 98 and are subjected to an elastic load directed towards axis B. With the abutment surface 107, the releasable retaining tabs 106 define gaps which are engaged by an annular upper flange 108 of the needle housing 104 to lock the needle assembly 105 in the opening 98. An electro-mechanical sensor (electric switch) 109 (FIG. 41), connected to the releasable retaining tabs 106, detects actuation of the tabs 106 by the needle housing 104 and sends an electric signal to the control unit 95.

Automatic connection of the needle 96 to the cartridge 83 is activated by the insertion of the needle assembly 105 between the tabs 106. This insertion, immediately detected by the sensor 109, causes the control unit 95 to activate the second actuator assembly 87 to move down the structure 82, 84, 86, 92 inside the device housing 81 from its retracted position. The retaining force exerted by the retaining tabs 106 on the needle housing 104 is sufficient for the needle housing 104 to remain locked in its position shown in FIG. 20 whilst the bottom end 100 of the cartridge holder 82 equipped with the intermediate fixing member 102 engages the needle support 99 (FIG. 21). Once the movable structure 82,84, 86,92 has reached a predetermined bottom position, in which the bottom end 100 of the cartridge holder 82 fully engages the needle support 99, thus connecting the needle 96 to the cartridge 83, the second actuator assembly 87 moves the structure 82, 84, 86, 92 back to its top, retracted position with the needle support 99 and the needle 96 connected to the cartridge 83, whilst the needle housing 104 is retained by the abutment surface 107 (FIG. 22).

Unlike the retaining elements 60 in the first embodiment, the retaining tabs 106 do not prevent the user from removing the needle housing 104 during connection of the needle 96 to the cartridge 83. However, any removal of the needle housing 104 during the connection process is detected by the sensor 109. If such a removal occurs, the control unit 95 immediately stops the connection process and controls the return of the movable structure 82, 84, 86, 92 to its top position. The user will then be proposed, via a display screen 110 (FIG. 41) provided on the injection device, to start a new connection process.

Figure 23:
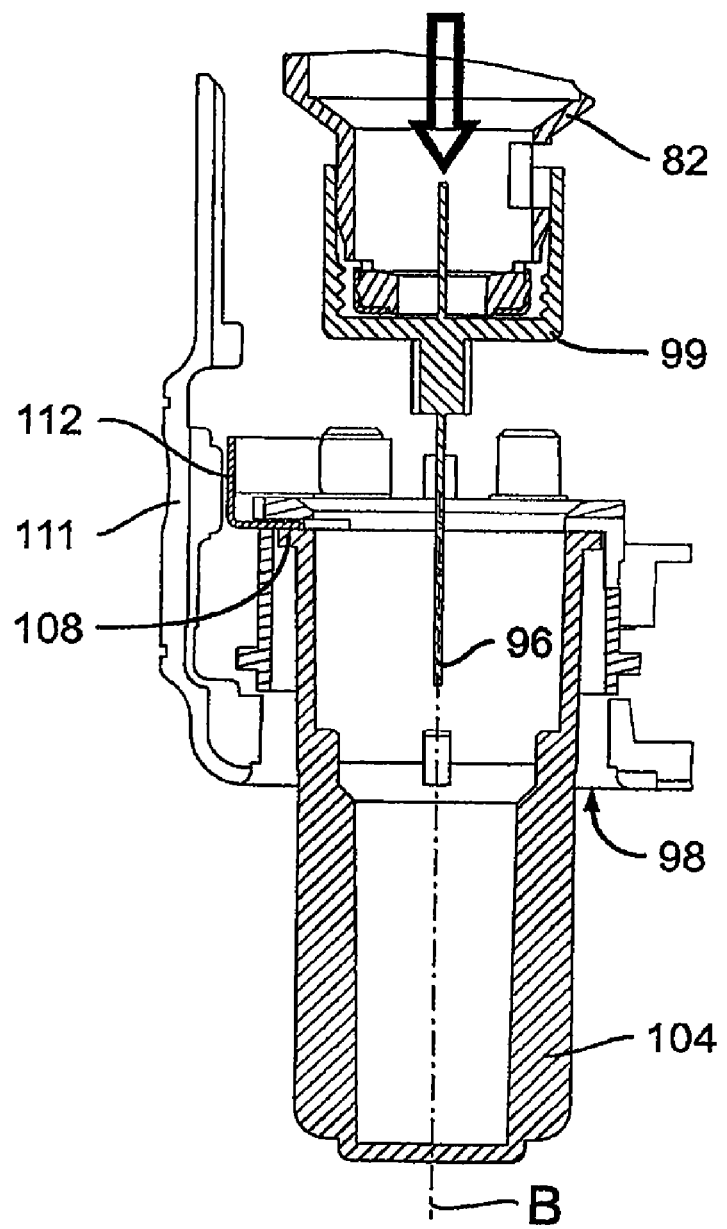

For detaching the needle 96 from the cartridge 83, the user inserts the empty needle housing 104 into the opening 98 up to engagement of the retaining means 106,107 by the needle housing 104. Actuation of the tabs 106 is detected by the sensor 109. This causes control unit 95 to activate the second actuator assembly 87 to move the structure 82, 84, 86, 92 down to a bottom position where the needle support 99 is fitted in the needle housing 104 (FIG. 23,24). The user may then actuate a needle release button 111 provided on the device housing 81 and connected to the control unit 95, to move a square retaining member 112 transversely to axis B up to a position where a leg 113 of the retaining member 112, inserted in a gap between the abutment surface 107 and the annular upper flange 108 of the needle housing 104, is above the upper end of the needle support 99 (FIG. 24). Thereafter, a reverse movement is imparted to the structure 82, 84,86, 92 while the needle support 99 and, with it, the needle 96 are retained by the retaining member 112, thereby detaching the needle support 99 and the needle 96 from the cartridge holder 82 and the cartridge 83 (FIG. 25). The user can then disengage the needle assembly 105 from the retaining tabs 106 and take it out of the injection device.

According to an advantageous aspect of the invention, the sensor means are provided in the injection device to detect connection of the needle 96 to the cartridge 83. These sensor means, visible in FIGS. 26-29, comprise an optical transmitter 114, such as a light-emitting diode, and first and second optical receivers 115,116, such as photodiodes, fixed to the interior face of the front or the back wall of the device housing 81, and a reflector 117, such as a mirror, fixed to the opposite, back or front wall of the device housing 81. Optical transmitter 114 is aligned with the first and second optical receivers 115,116 in a direction parallel to axis B and placed between them. When the cartridge holder 82, more precisely the movable structure 82, 84, 86, 92, is in the retracted position and no needle is connected to the cartridge 83 (FIG. 26), a first optical ray 118 forming part of a beam transmitted by the transmitter 114 passes a first time near the bottom end 100 of the cartridge holder 82, is reflected by the mirror 117 and passes a second time near the bottom end 100 to reach the first receiver 115, and a second optical beam 119 transmitted by the transmitter 114 passes a first time near the bottom end 100, is reflected by mirror 117 and passes a second time near the bottom end 100 to reach the second receiver 116. As apparent in FIG. 27, the cross-section of an upper portion of the bottom end 100 of the cartridge holder 82 is only partly circular, (i.e. bottom end 100 has a truncated, flat side portion 120), to let the first optical beam 118 pass. When the needle support 99, with the needle 96, is properly connected to the bottom end 100 of the cartridge holder 82, the optical beams 118, 119 are interrupted by the needle support 99 (FIG. 29). Receivers 115, 116 thus no longer receive the optical beams 118, 119. This is interpreted by the control unit 95 as implying that a needle 96 is properly connected to the cartridge 83. FIG. 28 shows an intermediate configuration where the needle support 99 and the needle 96 are only partly connected to the cartridge holder 82 and the cartridge 83. In this configuration, the second optical beam 119 is interrupted by the needle support 99 but the first optical beam 118, still reaches the first receiver 115. This is interpreted by the control unit 95 as implying that the needle 96 is only partly connected to the cartridge 83.

Thus, after the needle connection process described above, if the control unit 95 determines that no needle is connected to the cartridge 83 or that a needle is only partly connected to the cartridge 83, the user is not allowed to initiate the injection and is proposed to restart the needle connection process. Security of use of the injection device is thus increased.

Figure 30:
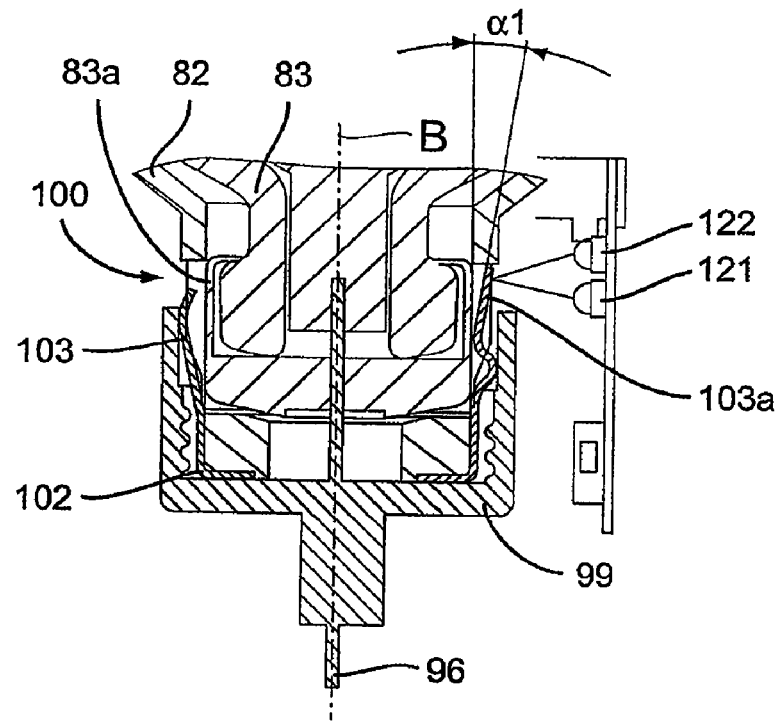
FIGS. 30 and 31 show alternative sensor means for sensing connection of the needle to the cartridge.
Figure 31:
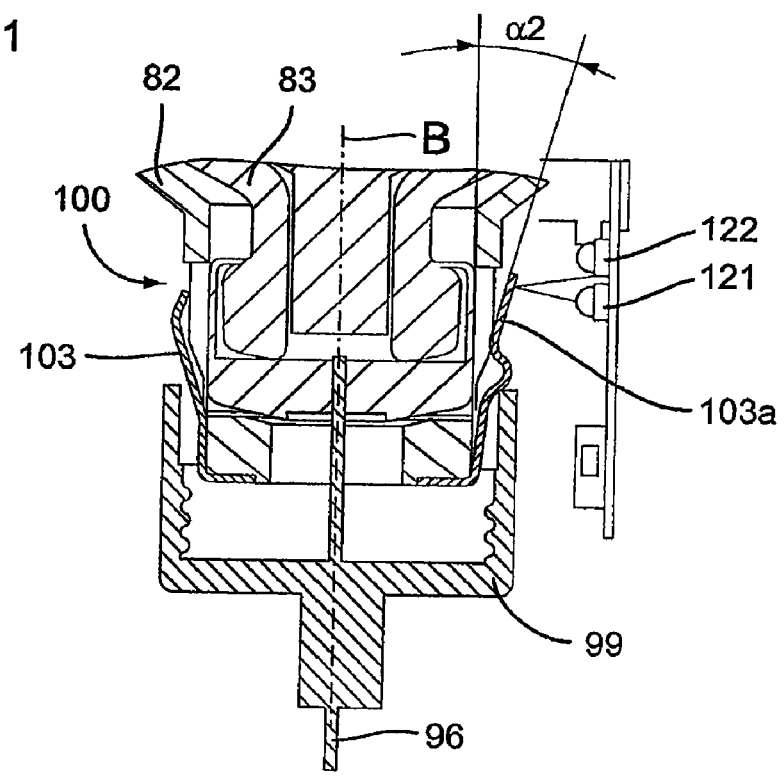
Figure 32:
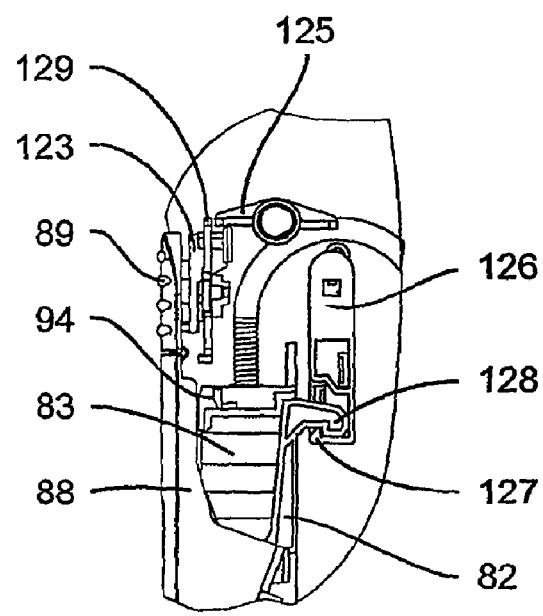
FIGS. 32-34 are respectively a front view, a side view and a partially cut side view with parts removed for clarity, of a portion of the injection device according to the second embodiment including a door opening mechanism and a door lock mechanism in a first configuration.
Figure 33:
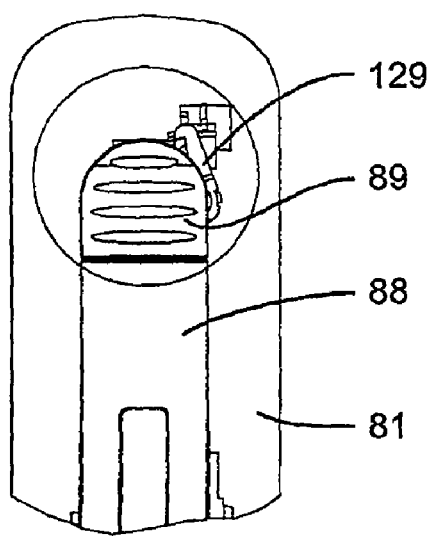
Figure 34:
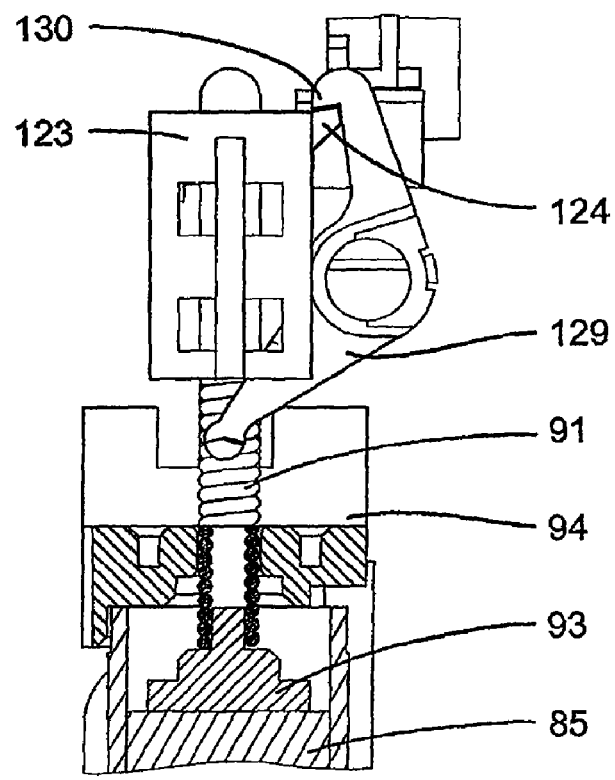

FIGS. 30 and 31 show alternative sensor means for detecting connection of the needle 96 to the cartridge 83. In this variant, one 103a, of the elastic flanges 103 of the intermediate fixing member 102 is longer than the other (s). When the cartridge holder 82 is in the retracted position and the needle 96 is properly connected to the cartridge 83, the longest elastic flange 103a, compressed between the needle support 99 and the bottom end 83a of the cartridge 83, has an end portion which projects outside the needle support 99 and defines a first angle a1 ??with axis B. In this configuration, an optical ray transmitted by an optical transmitter 121 is reflected by the projecting end portion of the flange 103a towards an optical receiver 122. Reception of a signal by the optical receiver 122 is interpreted by the control unit 95 as implying that the needle 96 is properly connected to the cartridge 83. If, on the other hand, the needle 96 is not properly connected to the cartridge 83, as shown in FIG. 31, then the projecting end portion of the flange 103a defines a second angle o2??, different from the first angle a1??, with axis B. In this case, the optical ray reflected by the projecting end portion of the flange 103a is not received by the receiver 122. This is interpreted by the control unit 95 as implying that no needle is connected to the cartridge 83 or that a needle is ill connected to the cartridge 83.

Returning to FIGS. 15 and 16, delivery of medication through the needle 96 is, as explained above, carried out by the piston 93 of the push member 84 which pushes the plunger 85 of the cartridge 83. During this process, the piston 93 and a portion of the tube 91 is within the cartridge 83. Piston 93 and the tube 91 remain within the cartridge 83 so long as doses of medication are left therein. Once all doses of medication contained in the cartridge 83 have been injected into a patient, the push member 84 is retracted outside the cartridge 83 to enable replacement of the latter (FIG. 15). A risk could however exist that, between two injections, the user opens door 88 to remove the cartridge 83 from the injection device whilst the push member 84 is still inside the cartridge 83. Such an operation could seriously damage the push member 84. In order to eliminate this risk, the present invention advantageously provides a lock mechanism which locks/unlocks the opening mechanism of the door 88 when the push member 84 is inside/outside the cartridge 83.

With reference to FIGS. 32-40, the opening mechanism of the door 88 comprises the opening button 89, which is slidable in a direction parallel to axis B, a lockable part 123 fixed to the opening button 89 inside the device housing 81 and comprising a flange 124, a lever 125 actuated by the lockable part 123 and a locking member 126 actuated by the lever 125. The lever 125 is mounted on an axis that is fixed relative to the device housing 81. Locking member 126 is mounted on the movable structure 82, 84, 86, 92 at a location situated on the opposite side of axis B with respect to the opening button 89 and so as to be slidable with respect to the movable structure 82, 84, 86, 92 in a direction parallel to axis B, and has a recess with a flange 127 designed to cooperate with a corresponding flange 128 of the cartridge holder 82.

The lock mechanism comprises a movable recessed part 94 and a lever 129 actuated by the recessed part 94 and having, at one of its end, a flange 130 designed to cooperate with the flange 124 of the lockable part 123. The lever 129 is mounted on an axis that is fixed relative to the device housing 81.

Recessed part 94 is movable along axis B and fixed to one end of a spring 131 (visible in FIGS. 13-16), the other end of which is fixed to the movable structure 82,84, 86, 92.

Figure 35:
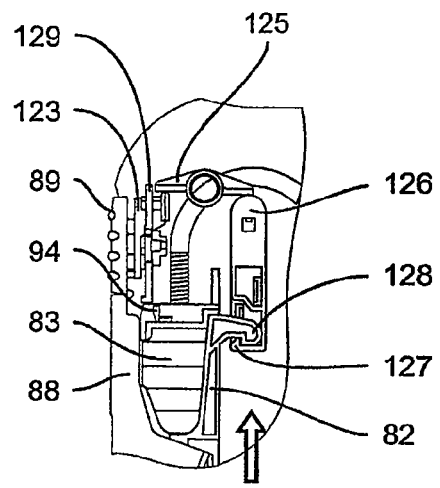
FIGS. 35-37 are respectively a front view, a side view and a partially cut side view with parts removed for clarity, of the portion of the injection device according to the second embodiment including the door opening mechanism and the door lock mechanism in a second configuration.
Figure 36:
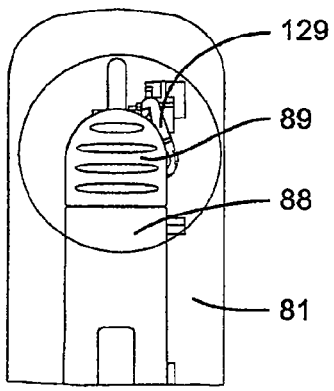
Figure 37:
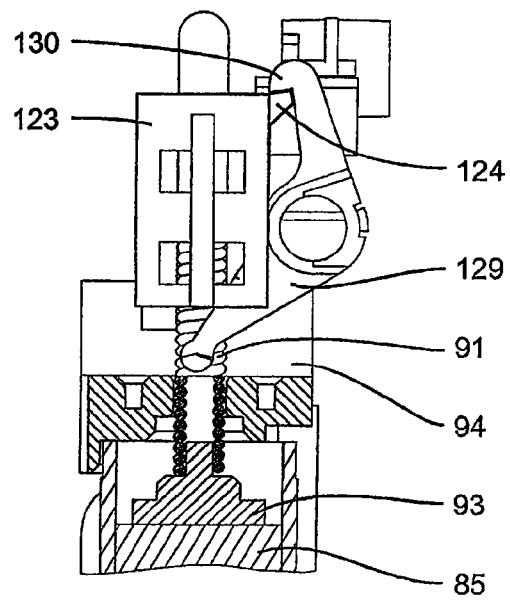
Figure 38:
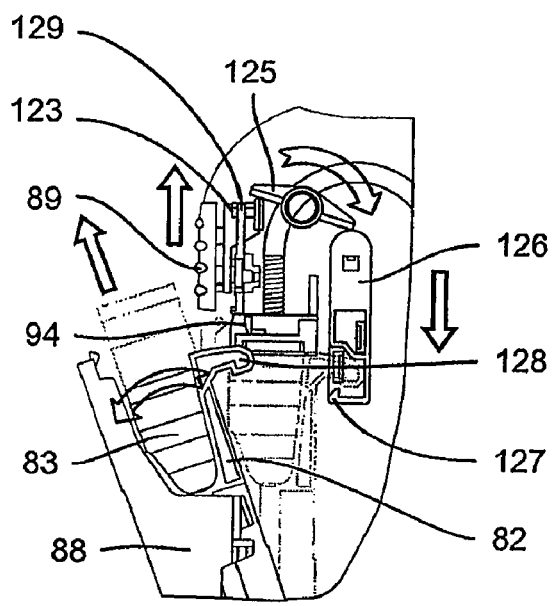
FIGS. 38-40 are respectively a front view, a side view and a partially cut side view with parts removed for clarity, of the portion of the injection device according to the second embodiment including the door opening mechanism and the door lock mechanism in a third configuration.
Figure 39:
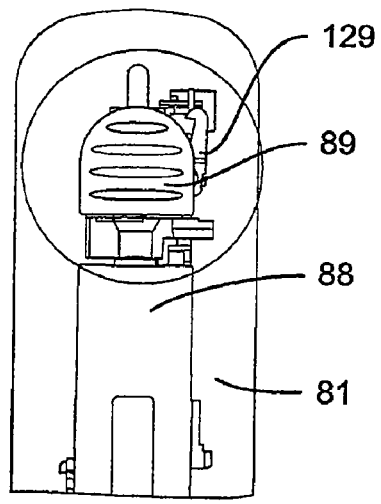
Figure 40:
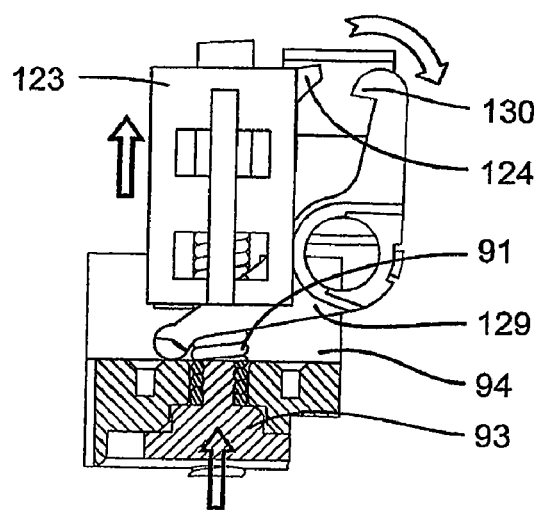

Operation of the opening and lock mechanisms is as follows: during injection of a medication dose (FIGS. 32-34), the movable structure 82, 84, 86, 92 is in a bottom position, the piston 93 of push member 84 is inside the cartridge 83 and the recessed part 94 is in a rest position, out of contact with the lever 129. In this configuration, the flange 130 of the second lever 129 engages the flange 124 of the lockable part 123 (FIG. 33, 34) so that the lockable part 123 and, with it, the opening button 89 are locked, (i.e. cannot be moved up), thus preventing the door 88 from being opened. Between two injections with the same cartridge 83, the movable structure 82, 84, 86, 92 is in its retracted position, the piston 93 of the push member 84 is inside the cartridge 83 and the recessed part 94 is in a rest position, out of contact with the lever 129 (FIGS. 35-37). In this configuration, the flange 130 of the second lever 129 still engages the flange 124 of the lockable part 123 (FIG. 37) so that the lockable part 123 and, with it, the opening button 89 remain locked, thus preventing the door 88 from being opened. Once all medication doses contained in the cartridge 83 have been injected, the movable structure 82, 84, 86, 92 and the piston 93 of the push member 84 are each retracted. During retraction of the push member 84, the piston 93 enters the recess of the recessed part 94 and pushes the recessed part 94 upwards against the action of the spring 131 so that the recessed part 94 comes into contact with the end of the second lever 129 opposite to the end having the flange 124 to rotate the lever 129 and thus disengage it from the lockable part 123 (FIG. 40). Door opening button 89 may then be slid upwards as shown in FIG. 38. Upwards motion of the opening button 89 causes the first lever 125 to rotate to move the locking member 126 down and thus disengage flange 128 of the cartridge holder 82 from the flange 127 of the locking member 126. Under the action of a spring, the door 88 and, with it, the cartridge holder 82 are then rotated about the pivot axis 90 to enable extraction of the cartridge 83 from the cartridge holder 82 (FIG. 38). Door opening button 89, the lever 125, the locking member 126 and the lever 129 are subjected to the action of respective springs which tend to maintain them in their rest position shown in FIGS. 32 to 34 or 35 to 37.

The invention claimed is:

1. A medication injection device comprising:
a housing;
a holder for receiving and holding in said housing a medication container an end of which is connectable to a needle;
control means;
means, controlled by said control means, for pushing liquid medication contained in said medication container out of said medication container through said needle; and
first optical sensor means, connected to said control means, for detecting proper connection of said needle to said medication container.

2. A device as claimed in claim 1, wherein said first optical sensor means comprise optical transmitter means and first optical receiver means arranged so that, when no needle is properly connected to said medication container, a first optical ray transmitted by said transmitter means passes near an end of a unit comprising said medication container and said holder to reach said first receiver means, and when said needle is properly connected to said medication container, said first optical ray is interrupted by a needle support supporting said needle.

3. A device as claimed in claim 2, wherein said end of said unit comprising said medication container and said holder is truncated to let said first optical ray pass when no needle is properly connected to said medication container.

4. A device as claimed in claim 1, comprising second sensor means for detecting partial connection of said needle to said medication container.

5. A device as claimed in claim 2, comprising second sensor means for detecting partial connection of said needle to said medication container.

6. A device as claimed in claim 5, wherein said second sensor means comprise said optical transmitter means and second optical receiver means arranged so that, when no needle is connected to said medication container, a second optical ray transmitted by said transmitter means passes near said end of said unit comprising said medication container and said holder to reach said second receiver means, and in a configuration where said needle is partly connected to said medication container, said second optical ray is interrupted by said needle support while said first optical ray still reaches said first receiver means.

7. A device as claimed in claim 1, wherein an end of a unit comprising said medication container and said holder is provided with at least one elastic flange for connection of a needle support supporting said needle to said end of said unit, and wherein said first optical sensor means comprise optical transmitter means and optical receiver means arranged so that, when said needle is properly connected to said medication container, a reflective portion of one of said elastic flange(s) reflects an optical ray transmitted by said transmitter means towards said receiver means, and when no needle is properly connected to said medication container, said reflective portion reflects said optical ray in a direction not corresponding to said receiver means.

* * * * *